United States Patent [19]

Gallie et al.

[11] Patent Number: 5,550,020
[45] Date of Patent: Aug. 27, 1996

[54] METHOD, REAGENTS AND KIT FOR DIAGNOSIS AND TARGETED SCREENING FOR RETINOBLASTOMA

[75] Inventors: Brenda L. Gallie, Toronto; James M. Dunn, Scarborough; John K. Stevens, Mississauga, all of Canada

[73] Assignees: Visible Genetics Inc.; HSC Research & Development, both of Toronto, Canada

[21] Appl. No.: 271,942

[22] Filed: Jul. 8, 1994

[51] Int. Cl.$^6$ ............... C12Q 1/68; C12P 19/34; C07H 21/04; C07H 21/02
[52] U.S. Cl. ............... 435/6; 435/91.2; 536/23.1; 536/24.3; 536/24.33
[58] Field of Search ............... 435/6, 91.2; 536/23.1, 536/24.3, 24.33

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 4,942,123 | 7/1990 | Lee et al. | 435/6 |
| 5,011,773 | 4/1991 | Lee et al. | 435/69.1 |
| 5,266,459 | 11/1993 | Beutler | 435/6 |

FOREIGN PATENT DOCUMENTS

| | | |
|---|---|---|
| 0259031 | 9/1988 | European Pat. Off. |
| 0390530 | 3/1990 | European Pat. Off. |
| 0539970 | 5/1993 | European Pat. Off. |
| 0608004 | 7/1994 | European Pat. Off. |
| 89/06703 | 7/1989 | WIPO |
| 90/12807 | 1/1990 | WIPO |
| 91/10734 | 1/1991 | WIPO |
| 92/01066 | 1/1992 | WIPO |
| 93/15227 | 5/1993 | WIPO |
| 93/18177 | 9/1993 | WIPO |
| 93/23539 | 11/1993 | WIPO |
| 94/01467 | 1/1994 | WIPO |

OTHER PUBLICATIONS

Shimizu et al., "Detection of Mutations of the RB1 Gene in Retinoblastoma Patients by Using Exon-by-Exon PCR-SSCP Analysis" *Am. J. Hum. Genet.* 54: 793–800 (1994).

Sachse et al., "DNA Aberrations at the Retinoblastoma Gene Locus in Human Squamous Cell Carcinomas of the Lung" *Oncogene* 9: 39–47 (1994).

Breslauer et al., "Predicting DNA Duplex Stability from base sequence", *Proc. Nat'l Acad. Sci. USA* 83: 3746=3750 (1986).

Canning et al., "Short direct repeats at the breakpoints of deletions of the retinoblastoma gene", *Proc. Nat'l Acad. Sci. USA* 86: 5044–5048 (1989).

(List continued on next page.)

*Primary Examiner*—W. Gary Jones
*Assistant Examiner*—Dianne Rees
*Attorney, Agent, or Firm*—Oppedahl & Larson

[57] ABSTRACT

Reliable and cost effective testing for mutations in the RB1 gene can be accomplished by quantitatively amplifying exons of the sample RB1 gene using primers complementary to intron regions flanking each exon; and then determining the lengths and/or quantities of the amplification products for each exon and comparing that length or quantity to the length or quantity of amplification products obtained when a wild-type RB1 gene is amplified using the same primers. Differences in length between an amplified sample exon and the corresponding amplified wild-type exon reflect the occurrence of an insertion or deletion mutation in the sample RB1 gene. Differences in quantity reflect the complete absence of an exon, or heterozygosity for a mutant exon. Next, the nucleic acid sequence of each exon found to contain an insertion or deletion mutation is determined, or of all exons in the event no insertion or deletion mutations are identified. Preferably, the amplification of the exons is multiplexed so that more than one exon is amplified in a single vessel using sets of primers which provide gene fragments of distinctive lengths when used to amplify a normal RB1 gene.

137 Claims, 3 Drawing Sheets

OTHER PUBLICATIONS

DerKinderen et al., "Early Diagnosis of Bilateral Retinoblastoma Reduces Death and Blindness", *Int. J. Cancer* 44: 35–439 (1989).

Dryja, T. P., "DNA Testing for Retinoblastoma", *Arch. Ophthalmol.* 109: 1210 (1991).

Dryja et al., "Molecular etiology of low-penetrance retinoblastoma in two pedigrees", *Amer. J. Genetics* 52: 1122–1128 (1993).

Dunn, et al., "Mutations in the RB1 Gene and Their Effects on Transcription", *Molecular and Cellular Biology* 9: 4596–4604 (1989).

Dunn et al., "Identification of Germline and Somatic Mutations Affecting the Retinoblastoma Gene", *Science* 241: 1797–1800 (1988).

Friend et al., "A human DNA Segment with Properties of the Gene that Predisposes to Retinoblastoma and Osteosarcoma" *Nature* 323:643–6 (1986).

Gallie, B. L. "The Misadventures of RB1", in *Causes and Consequences of Chromsomal Aberrations*, pp. 429–446, CRC Press (1993).

Goddard et al., "Use of the RB1 cDNA as a diagnostic prove in retinoblastoma families", *Clin. Genetics* 37: 117–26 (1990).

Horsthhemke et al., "Early diagnosis of hereditary retinoblastoma by detection of molecular deletions at gene locus", *Lancet* 1: 511–512 (1987).

Horsthemke et al., "Detection of submicroscopic deletions and a DNA polymorphism at the retinoblastoma locus" *Human Genetics* 76: 257–61 (1987).

Lee et al., "Diverse mutations lead to inactivation of the retinoblastoma gene", *Prog. Clin. Biol. Res.* 362: 221–240 (1991).

Lee et al., "Human retinoblastoma susceptibility gene: cloning, identification and sequence", *Science* 235: 1394–1399 (1987).

Lee et al. "The retinoblastoma susceptibility gene encodes a nuclear phosphoprotein associated with DNA binding activity", *Nature* 329: 642–645 (1987).

Lohmann et al., "Detection of small RB1 deletions in retinoblastoma by multiplex PCR and high resolution gel electrophoresis" *Human Genetics* 89: 49–53 (1992).

Orita, et al., "Detection of polymorphisms of human DNA by gel electrophoresis as single-strand conformation polymorphisms", *Proc. Nat'l. Acad. Sci. USA* 86:2766–2770 (1989).

Rychlik, W., "Selection of Primers for Polymerase Chain Reaction", *Methods in Molecular Biology*, vol. 15: *PCR Protocols: Current Methods and Applications*, pp. 31–40 (1993).

Sasano et al., "An analysis of abnormalities of the retinoblastoma gene in human ovarian and endometrial carcinoma", *Cancer* 66: 2150–2154 (1990).

Savard–McQuigge et al., *Your Child Has Retinoblastoma*, Canadian Cancer Society (1992).

Toguchida et al., "Complete genomic sequence of the human retinoblastoma susceptibility gene", *Genomics* 17L 535–543 (1993) found by DR.

Wiggs, et al., "Prediction of the risk of hereditary retinoblastoma using DNA polymorphisms within the retinoblastoma gene", *N. Engl. J. Med.* 318: 151–157 (1988).

Yandell et al., "Oncogenic point mutations in the human retinoblastoma gene: their application to genetic counseling", *N. Engl. J. Med.* 321: 1689–1694 (1989).

Toguchida et al. Genomics 17:535–543. 1993.

Lohmann et al. Human Genet. 89: 49–53, 1992.

McConkey, In Human Genetics, The Molecular Revolution, Jones and Bartlett Publishers NY, 1993, pp. 192–197.

Innis et al. PCR Protocols: A guide to Methods and Applications, Academic Press, 1990, pp. 3–13, 70–76.

Dunn et al., "Sequence based diagnosis of retinoblastoma", Keystone Symposium on Tumor Suppressor genes, Taos, New Mexico, Feb. 13–20, 1994, J. Cellular Biochem Supp: 199 (1994).

SEQUENCE LISTING ( 1 ) GENERAL INFORMATION:

( i i i ) NUMBER OF SEQUENCES: 123

( 2 ) INFORMATION FOR SEQ ID NO:1:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 2 of human RB1 gene ( x i ) SEQUENCE DESCRIPTION: SEQ ID NO:1:

ACTGTGTGGT ATCCTTATTT TG          22

( 2 ) INFORMATION FOR SEQ ID NO:2:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 2 of human RB1 gene ( x i ) SEQUENCE DESCRIPTION: SEQ ID NO:2:

ATAGTGATTT GAAGTTGGTT TTA          23

( 2 ) INFORMATION FOR SEQ ID NO:3:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
    (A) ORGANISM: human (ix) FEATURE:
    (A) NAME/KEY: primer for exon 3 of human RB1 gene (xi) SEQUENCE DESCRIPTION: SEQ ID NO:3:

ATACAGTTTT AACATAGTAT CCA            23

(2) INFORMATION FOR SEQ ID NO:4:

(i) SEQUENCE CHARACTERISTICS:
    (A) LENGTH: 22
    (B) TYPE: nucleic acid
    (C) STRANDEDNESS: single
    (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
    (A) ORGANISM: human (ix) FEATURE:
    (A) NAME/KEY: primer for exon 3 of human RB1 gene (xi) SEQUENCE DESCRIPTION: SEQ ID NO:4:

AAGTCTATTG AGAGGAAAAT CC             22

(2) INFORMATION FOR SEQ ID NO:5:

(i) SEQUENCE CHARACTERISTICS:
    (A) LENGTH: 22
    (B) TYPE: nucleic acid
    (C) STRANDEDNESS: single
    (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
    (A) ORGANISM: human (ix) FEATURE:
    (A) NAME/KEY: primer for exon 5 of human RB1 gene (xi) SEQUENCE DESCRIPTION: SEQ ID NO:5:

CTACTATGAC TTCTAAATTA CG             22

(2) INFORMATION FOR SEQ ID NO:6:

(i) SEQUENCE CHARACTERISTICS:
    (A) LENGTH: 22
    (B) TYPE: nucleic acid
    (C) STRANDEDNESS: single
    (D) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 5 of human RB1 gene ( x i ) SEQUENCE DESCRIPTION: SEQ ID NO:6:

TCAAGATGTT TGAGATTATT CC    22

( 2 ) INFORMATION FOR SEQ ID NO:7:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 13 of human RB1 gene ( x i ) SEQUENCE DESCRIPTION: SEQ ID NO:7:

TGCTTATGTT CAGTAGTTGT G    21

( 2 ) INFORMATION FOR SEQ ID NO:8:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 13 of human RB1 gene ( x i ) SEQUENCE DESCRIPTION: SEQ ID NO:8:

TAATGGGGTG GGAGGTAGTT T    21

( 2 ) INFORMATION FOR SEQ ID NO:9:

( i ) SEQUENCE CHARACTERISTICS:
        ( A ) LENGTH: 22
        ( B ) TYPE: nucleic acid
        ( C ) STRANDEDNESS: single (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
    (A) ORGANISM: human (i x) FEATURE:
    (A) NAME/KEY: primer for exon 25 of human RB1 gene (x i) SEQUENCE DESCRIPTION: SEQ ID NO:9:

TCAAACTATA ACTTGAGGTT GC      22

(2) INFORMATION FOR SEQ ID NO:10:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (i x) FEATURE:
        (A) NAME/KEY: primer for exon 25 of human RB1 gene (x i) SEQUENCE DESCRIPTION: SEQ ID NO:10:

AAAGAAATTG GTATAAGCCA GG      22

(2) INFORMATION FOR SEQ ID NO:11:

(i) SEQUENCE CHARACTERISTICS:
        (A) LENGTH: 19
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (v i i i) POSITION IN GENOME:
        (A) CHROMOSOME/SEGMENT: chromosome 15

(i x) FEATURE:
        (A) NAME/KEY: primer amplification of control region of chromsome 15

(x i) SEQUENCE DESCRIPTION: SEQ ID NO:11:

CTCACCCGCA CCTAAGTTT      19

(2) INFORMATION FOR SEQ ID NO:12:

(i) SEQUENCE CHARACTERISTICS:
  (A) LENGTH: 21
  (B) TYPE: nucleic acid
  (C) STRANDEDNESS: single
  (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
  (A) ORGANISM: human (viii) POSITION IN GENOME:
  (A) CHROMOSOME/SEGMENT: chromosome 15

(ix) FEATURE:
  (A) NAME/KEY: primer amplification of control region of chromsome 15

(xi) SEQUENCE DESCRIPTION: SEQ ID NO:12:

CCAGGATGAG AGCGGATGGC A                 21

(2) INFORMATION FOR SEQ ID NO:13:

(i) SEQUENCE CHARACTERISTICS:
  (A) LENGTH: 19
  (B) TYPE: nucleic acid
  (C) STRANDEDNESS: single
  (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
  (A) ORGANISM: human (ix) FEATURE:
  (A) NAME/KEY: primer for exon 1 of human RB1 gene (xi) SEQUENCE DESCRIPTION: SEQ ID NO:13:

GCCCCAGTTC CCCACAGAC                    19

(2) INFORMATION FOR SEQ ID NO:14:

(i) SEQUENCE CHARACTERISTICS:
  (A) LENGTH: 19
  (B) TYPE: nucleic acid
  (C) STRANDEDNESS: single
  (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
  (A) ORGANISM: human (ix) FEATURE:
  (A) NAME/KEY: primer for exon 1 of human RB1 gene (xi) SEQUENCE DESCRIPTION: SEQ ID NO:14:

ACCCCTCGCC CAAGAACCC 19

( 2 ) INFORMATION FOR SEQ ID NO:15:

( i ) SEQUENCE CHARACTERISTICS:
( A ) LENGTH: 21
( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
( A ) ORGANISM: human ( i x ) FEATURE:
( A ) NAME/KEY: primer for exon 8 of human RB1 gene ( x i ) SEQUENCE DESCRIPTION: SEQ ID NO:15:

TCTAATGAAA CCTAATAAGT A 21

( 2 ) INFORMATION FOR SEQ ID NO:16:

( i ) SEQUENCE CHARACTERISTICS:
( A ) LENGTH: 21
( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
( A ) ORGANISM: human ( i x ) FEATURE:
( A ) NAME/KEY: primer for exon 8 of human RB1 gene ( x i ) SEQUENCE DESCRIPTION: SEQ ID NO:16:

TGCTCATAAC AAAAGAAGTA A 21

( 2 ) INFORMATION FOR SEQ ID NO:17:

( i ) SEQUENCE CHARACTERISTICS:
( A ) LENGTH: 21
( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
( A ) ORGANISM: human ( i x ) FEATURE:
( A ) NAME/KEY: primer for exon 18 of human RB1 gene ( x i ) SEQUENCE DESCRIPTION: SEQ ID NO:17:

TTTTTGTGTG TGGGAAGTAC A                  2 1

( 2 ) INFORMATION FOR SEQ ID NO:18:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 18 of human RB1 gene ( x i ) SEQUENCE DESCRIPTION: SEQ ID NO:18:

ATTCTATTCC CTACAGTTTC TT                 2 2

( 2 ) INFORMATION FOR SEQ ID NO:19:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 21 of human RB1 gene ( x i ) SEQUENCE DESCRIPTION: SEQ ID NO:19:

GGCTAAAAGA AAGAAAATGG                    2 0

( 2 ) INFORMATION FOR SEQ ID NO:20:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 21 of human RB1 gene ( x i ) SEQUENCE DESCRIPTION: SEQ ID NO:20:

TTACCTATGT TATGTTATGG  20

( 2 ) INFORMATION FOR SEQ ID NO:21:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 22 of human RB1 gene ( x i ) SEQUENCE DESCRIPTION: SEQ ID NO:21:

TATGTGCTTC TTACCAGTCA AA  22

( 2 ) INFORMATION FOR SEQ ID NO:22:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 23 of human RB1 gene ( x i ) SEQUENCE DESCRIPTION: SEQ ID NO:22:

GGAGTCATTT TTGTTGGTGT TG  22

( 2 ) INFORMATION FOR SEQ ID NO:23:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:

( A ) NAME/KEY: primer for exon 23 of human RB1 gene ( x i ) SEQUENCE DESCRIPTION: SEQ ID NO:23:

AATCTAATGT AATGGGTCCA CC                22

( 2 ) INFORMATION FOR SEQ ID NO:24:

( i ) SEQUENCE CHARACTERISTICS:
                    ( A ) LENGTH: 22
                    ( B ) TYPE: nucleic acid
                    ( C ) STRANDEDNESS: single
                    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
                    ( A ) ORGANISM: human ( i x ) FEATURE:
                    ( A ) NAME/KEY: primer for exon 23 of human RB1 gene ( x i ) SEQUENCE DESCRIPTION: SEQ ID NO:24:

ATCAAAATAA TCCCCCTCTC AT                22

( 2 ) INFORMATION FOR SEQ ID NO:25:

( i ) SEQUENCE CHARACTERISTICS:
                    ( A ) LENGTH: 20
                    ( B ) TYPE: nucleic acid
                    ( C ) STRANDEDNESS: single
                    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
                    ( A ) ORGANISM: human ( i x ) FEATURE:
                    ( A ) NAME/KEY: primer for exon 6 of human RB1 gene ( x i ) SEQUENCE DESCRIPTION: SEQ ID NO:25:

AAAGAAACAC CCAAAAGATA                   20

( 2 ) INFORMATION FOR SEQ ID NO:26:

( i ) SEQUENCE CHARACTERISTICS:
                    ( A ) LENGTH: 22
                    ( B ) TYPE: nucleic acid
                    ( C ) STRANDEDNESS: single
                    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
                    ( A ) ORGANISM: human ( i x ) FEATURE:
    ( A ) NAME/KEY: primer for exon 6 of human RB1 gene ( x i ) SEQUENCE DESCRIPTION: SEQ ID NO:26:

TAATAAGCCA AGCAGAGAAT GA          22

( 2 ) INFORMATION FOR SEQ ID NO:27:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 7 of human RB1 gene ( x i ) SEQUENCE DESCRIPTION: SEQ ID NO:27:

TTATGGATAT ACTCTACCCT GC          22

( 2 ) INFORMATION FOR SEQ ID NO:28:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 7 of human RB1 gene ( x i ) SEQUENCE DESCRIPTION: SEQ ID NO:28:

CCTCCATTTG TTGTATTTTG AC          22

( 2 ) INFORMATION FOR SEQ ID NO:29:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
  ( A ) NAME/KEY: primer for exon 9 of human RB1 gene ( x i ) SEQUENCE DESCRIPTION: SEQ ID NO:29:

TCAAGAGTCA AGAGATTAGA               20

( 2 ) INFORMATION FOR SEQ ID NO:30:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 9 of human RB1 gene ( x i ) SEQUENCE DESCRIPTION: SEQ ID NO:30:

ATTATCCTCC CTCCACAGTC TC            22

( 2 ) INFORMATION FOR SEQ ID NO:31:

( i ) SEQUENCE CHARACTERISTICS:
    ( A ) LENGTH: 19
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 10 of human RB1 gene ( x i ) SEQUENCE DESCRIPTION: SEQ ID NO:31:

GTGCTGAGAG ATGTAATGA                19

( 2 ) INFORMATION FOR SEQ ID NO:32:

( i ) SEQUENCE CHARACTERISTICS:
    ( A ) LENGTH: 19
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:

(A) ORGANISM: human (ix) FEATURE:
(A) NAME/KEY: primer for exon 10 of human RB1 gene (xi) SEQUENCE DESCRIPTION: SEQ ID NO:32:

TATCTAAAGC AAATCAATC                    19

(2) INFORMATION FOR SEQ ID NO:33:

(i) SEQUENCE CHARACTERISTICS:
(A) LENGTH: 20
(B) TYPE: nucleic acid
(C) STRANDEDNESS: single
(D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
(A) ORGANISM: human (ix) FEATURE:
(A) NAME/KEY: primer for exon 11 of human RB1 gene (xi) SEQUENCE DESCRIPTION: SEQ ID NO:33:

TGAGACAACA GAAGCATTAT                    20

(2) INFORMATION FOR SEQ ID NO:34:

(i) SEQUENCE CHARACTERISTICS:
(A) LENGTH: 21
(B) TYPE: nucleic acid
(C) STRANDEDNESS: single
(D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
(A) ORGANISM: human (ix) FEATURE:
(A) NAME/KEY: primer for exon 11 of human RB1 gene (xi) SEQUENCE DESCRIPTION: SEQ ID NO:34:

TGAACAAATC TGAAACACTA T                    21

(2) INFORMATION FOR SEQ ID NO:35:

(i) SEQUENCE CHARACTERISTICS:
(A) LENGTH: 22
(B) TYPE: nucleic acid
(C) STRANDEDNESS: single
(D) TOPOLOGY: linear (ii) MOLECULE TYPE: genomic DNA (iii) HYPOTHETICAL: no (iv) ANTI-SENSE: no (v) FRAGMENT TYPE: internal (v i) ORIGINAL SOURCE:
    (A) ORGANISM: human (i x) FEATURE:
    (A) NAME/KEY: primer for exon 12 of human RB1 gene (x i) SEQUENCE DESCRIPTION: SEQ ID NO:35:

CTCCCTTCAT TGCTTAACAC AT                22

(2) INFORMATION FOR SEQ ID NO:36:

(i) SEQUENCE CHARACTERISTICS:
        (A) LENGTH: 21
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (i x) FEATURE:
        (A) NAME/KEY: primer for exon 12 of human RB1 gene (x i) SEQUENCE DESCRIPTION: SEQ ID NO:36:

AAAAGCAAGA AAAGATTATG G                 21

(2) INFORMATION FOR SEQ ID NO:37:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (i x) FEATURE:
        (A) NAME/KEY: primer for exon 27 of human RB1 gene (x i) SEQUENCE DESCRIPTION: SEQ ID NO:37:

ACTTACCCAG TACCATCAAT GC                22

(2) INFORMATION FOR SEQ ID NO:38:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
    (A) ORGANISM: human (i x) FEATURE:
    (A) NAME/KEY: primer for exon 27 of human RB1 gene (x i) SEQUENCE DESCRIPTION: SEQ ID NO:38:

TCAAGTGGCT TAGGAATCAC CC        22

(2) INFORMATION FOR SEQ ID NO:39:

(i) SEQUENCE CHARACTERISTICS:
        (A) LENGTH: 18
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (i x) FEATURE:
        (A) NAME/KEY: primer for exon 4 of human RB1 gene (x i) SEQUENCE DESCRIPTION: SEQ ID NO:39:

TTGAAAACGA AATAACAC        18

(2) INFORMATION FOR SEQ ID NO:40:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (i x) FEATURE:
        (A) NAME/KEY: primer for exon 4 of human RB1 gene (x i) SEQUENCE DESCRIPTION: SEQ ID NO:40:

ATAAAAAATC AGAGTGTAAC CC        22

(2) INFORMATION FOR SEQ ID NO:41:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 14 of human RB1 gene ( x i ) SEQUENCE DESCRIPTION: SEQ ID NO:41:

GTGATTTTCT AAAATAGCAG GC    22

( 2 ) INFORMATION FOR SEQ ID NO:42:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 14 of human RB1 gene ( x i ) SEQUENCE DESCRIPTION: SEQ ID NO:42:

CCAGGATGAT CTTGATGCC    19

( 2 ) INFORMATION FOR SEQ ID NO:43:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 20 of human RB1 gene ( x i ) SEQUENCE DESCRIPTION: SEQ ID NO:43:

GAAAAGAGTG GTAGAAAAGA GG    22

( 2 ) INFORMATION FOR SEQ ID NO:44:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no (v) FRAGMENT TYPE: internal (vi) ORIGINAL SOURCE:
    (A) ORGANISM: human (ix) FEATURE:
    (A) NAME/KEY: primer for exon 20 of human RB1 gene (xi) SEQUENCE DESCRIPTION: SEQ ID NO:44:

TAACAAGTAA GTAGGGAGGA GA        22

(2) INFORMATION FOR SEQ ID NO:45:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 24 of human RB1 gene (xi) SEQUENCE DESCRIPTION: SEQ ID NO:45:

GTATTTATGC TCATCTCTGC        20

(2) INFORMATION FOR SEQ ID NO:46:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 24 of human RB1 gene (xi) SEQUENCE DESCRIPTION: SEQ ID NO:46:

GTGTTTGAAT AACTGCATTT GG        22

(2) INFORMATION FOR SEQ ID NO:47:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: genomic DNA (iii) HYPOTHETICAL: no (i v) ANTI-SENSE: no (v) FRAGMENT TYPE: internal (v i) ORIGINAL SOURCE:
    (A) ORGANISM: human (i x) FEATURE:
    (A) NAME/KEY: primer for exon 26 of human RB1 gene (x i) SEQUENCE DESCRIPTION: SEQ ID NO:47:

CGAAAGCATC ATAGTTACTG G      21

(2) INFORMATION FOR SEQ ID NO:48:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (i x) FEATURE:
        (A) NAME/KEY: primer for exon 26 of human RB1 gene (x i) SEQUENCE DESCRIPTION: SEQ ID NO:48:

ATATAACGAA AAGACTTCTT GC      22

(2) INFORMATION FOR SEQ ID NO:49:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (i x) FEATURE:
        (A) NAME/KEY: primer for exons 15 and 16 of human RB1 gene (x i) SEQUENCE DESCRIPTION: SEQ ID NO:49:

CAATGCTGAC ACAAATAAGG TT      22

(2) INFORMATION FOR SEQ ID NO:50:

(i) SEQUENCE CHARACTERISTICS:
        (A) LENGTH: 20
        (B) TYPE: nucleic acid
        (C) STRANDEDNESS: single
        (D) TOPOLOGY: linear (i i) MOLECULE TYPE: genomic DNA (i i i) HYPOTHETICAL: no ( i v ) ANTI-SENSE: no ( v ) FRAGMENT TYPE: internal ( v i ) ORIGINAL SOURCE:
  ( A ) ORGANISM: human ( i x ) FEATURE:
  ( A ) NAME/KEY: primer for exons 15 and 16 of human RB1 gene ( x i ) SEQUENCE DESCRIPTION: SEQ ID NO:50:

CCCCCGACCA AAGAAACACA 20

( 2 ) INFORMATION FOR SEQ ID NO:51:

( i ) SEQUENCE CHARACTERISTICS:
  ( A ) LENGTH: 22
  ( B ) TYPE: nucleic acid
  ( C ) STRANDEDNESS: single
  ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
  ( A ) ORGANISM: human ( i x ) FEATURE:
  ( A ) NAME/KEY: primer for exon 17 of human RB1 gene ( x i ) SEQUENCE DESCRIPTION: SEQ ID NO:51:

ACCTTTCTAC TGTTTTCTTT GT 22

( 2 ) INFORMATION FOR SEQ ID NO:52:

( i ) SEQUENCE CHARACTERISTICS:
  ( A ) LENGTH: 20
  ( B ) TYPE: nucleic acid
  ( C ) STRANDEDNESS: single
  ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
  ( A ) ORGANISM: human ( i x ) FEATURE:
  ( A ) NAME/KEY: primer for exon 17 of human RB1 gene ( x i ) SEQUENCE DESCRIPTION: SEQ ID NO:52:

AAACACCTCT CACTAACAAT 20

( 2 ) INFORMATION FOR SEQ ID NO:53:

( i ) SEQUENCE CHARACTERISTICS:
  ( A ) LENGTH: 22
  ( B ) TYPE: nucleic acid
  ( C ) STRANDEDNESS: single
  ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 19 of human RB1 gene ( x i ) SEQUENCE DESCRIPTION: SEQ ID NO:53:

TGTATAATCT GTGATTCTTA GC          22

( 2 ) INFORMATION FOR SEQ ID NO:54:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 19 of human RB1 gene ( x i ) SEQUENCE DESCRIPTION: SEQ ID NO:54:

GCAACATTAT CATTTCCATT TT          22

( 2 ) INFORMATION FOR SEQ ID NO:55:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for promtoer region of human RB1 gene ( x i ) SEQUENCE DESCRIPTION: SEQ ID NO:55:

CCCACCAGAC TCTTTGTA          18

( 2 ) INFORMATION FOR SEQ ID NO:56:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) MOLECULE TYPE: genomic DNA (i i i) HYPOTHETICAL: no (i v) ANTI-SENSE: no (v) FRAGMENT TYPE: internal (v i) ORIGINAL SOURCE:
 (A) ORGANISM: human (i x) FEATURE:
 (A) NAME/KEY: primer for promoter region of human RB1 gene (x i) SEQUENCE DESCRIPTION: SEQ ID NO:56:

ACGTCCCTG AGAAAAACCG GA            22

(2) INFORMATION FOR SEQ ID NO:57:

(i) SEQUENCE CHARACTERISTICS:
 (A) LENGTH: 21
 (B) TYPE: nucleic acid
 (C) STRANDEDNESS: single
 (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
 (A) ORGANISM: human (i x) FEATURE:
 (A) NAME/KEY: primer for exon 1 of human RB1 gene (x i) SEQUENCE DESCRIPTION: SEQ ID NO:57:

GCCCCAGTTC CCCACAGACG C            21

(2) INFORMATION FOR SEQ ID NO:58:

(i) SEQUENCE CHARACTERISTICS:
 (A) LENGTH: 22
 (B) TYPE: nucleic acid
 (C) STRANDEDNESS: single
 (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
 (A) ORGANISM: human (i x) FEATURE:
 (A) NAME/KEY: primer for exon 2 of human RB1 gene (x i) SEQUENCE DESCRIPTION: SEQ ID NO:58:

TCCTCTGGGT AATGGAATTA TT            22

(2) INFORMATION FOR SEQ ID NO:59:

(i) SEQUENCE CHARACTERISTICS:
 (A) LENGTH: 22
 (B) TYPE: nucleic acid
 (C) STRANDEDNESS: single
 (D) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 4 of human RB1 gene ( x i ) SEQUENCE DESCRIPTION: SEQ ID NO:59:

AGTAGTGATT TGATGTAGAG CT    22

( 2 ) INFORMATION FOR SEQ ID NO:60:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 4 of human RB1 gene ( x i ) SEQUENCE DESCRIPTION: SEQ ID NO:60:

ATCAAGATGT TTGAGATTAT TCC    23

( 2 ) INFORMATION FOR SEQ ID NO:61:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 6 of human RB1 gene ( x i ) SEQUENCE DESCRIPTION: SEQ ID NO:61:

CACAAAAAGA AACACCCAAA AG    22

( 2 ) INFORMATION FOR SEQ ID NO:62:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 7 of human RB1 gene ( x i ) SEQUENCE DESCRIPTION: SEQ ID NO:62:

TACTCTACCC TGCGATTTTC TC        22

( 2 ) INFORMATION FOR SEQ ID NO:63:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 9 of human RB1 gene ( x i ) SEQUENCE DESCRIPTION: SEQ ID NO:63:

ATGGGGATT GACACCTCTA AC        22

( 2 ) INFORMATION FOR SEQ ID NO:64:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 10 of human RB1 gene ( x i ) SEQUENCE DESCRIPTION: SEQ ID NO:64:

TAATGAAATC TGTGCCTCTG        20

( 2 ) INFORMATION FOR SEQ ID NO:65:

( i ) SEQUENCE CHARACTERISTICS:
        ( A ) LENGTH: 22
        ( B ) TYPE: nucleic acid
        ( C ) STRANDEDNESS: single ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
            ( A ) ORGANISM: human ( i x ) FEATURE:
            ( A ) NAME/KEY: primer for exon 11 of human RB1 gene ( x i ) SEQUENCE DESCRIPTION: SEQ ID NO:65:

TATGATTTTA TGAGACAACA GA                 22

( 2 ) INFORMATION FOR SEQ ID NO:66:

( i ) SEQUENCE CHARACTERISTICS:
            ( A ) LENGTH: 21
            ( B ) TYPE: nucleic acid
            ( C ) STRANDEDNESS: single
            ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
            ( A ) ORGANISM: human ( i x ) FEATURE:
            ( A ) NAME/KEY: primer for exon 12 of human RB1 gene ( x i ) SEQUENCE DESCRIPTION: SEQ ID NO:66:

AACTTGGGAG ATTGAAAACA T                  21

( 2 ) INFORMATION FOR SEQ ID NO:67:

( i ) SEQUENCE CHARACTERISTICS:
            ( A ) LENGTH: 22
            ( B ) TYPE: nucleic acid
            ( C ) STRANDEDNESS: single
            ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
            ( A ) ORGANISM: human ( i x ) FEATURE:
            ( A ) NAME/KEY: primer for exon 14 of human RB1 gene ( x i ) SEQUENCE DESCRIPTION: SEQ ID NO:67:

AAAGCAGGAG GATCTCTTGA GC                 22

( 2 ) INFORMATION FOR SEQ ID NO:68:

( i ) SEQUENCE CHARACTERISTICS:
            ( A ) LENGTH: 21
            ( B ) TYPE: nucleic acid ( C ) STRANDEDNESS: single
( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
( A ) ORGANISM: human ( i x ) FEATURE:
( A ) NAME/KEY: primer for exons 15 and 16 of human RB1 gene ( x i ) SEQUENCE DESCRIPTION: SEQ ID NO:68:

CTCCCCCGAC CACCGAAACA C  21

( 2 ) INFORMATION FOR SEQ ID NO:69:

( i ) SEQUENCE CHARACTERISTICS:
( A ) LENGTH: 21
( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
( A ) ORGANISM: human ( i x ) FEATURE:
( A ) NAME/KEY: primer for exon 17 of human RB1 gene ( x i ) SEQUENCE DESCRIPTION: SEQ ID NO:69:

ATTAGATGGT TTAGGGTGCT C  21

( 2 ) INFORMATION FOR SEQ ID NO:70:

( i ) SEQUENCE CHARACTERISTICS:
( A ) LENGTH: 19
( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
( A ) ORGANISM: human ( i x ) FEATURE:
( A ) NAME/KEY: primer for exon 18 of human RB1 gene ( x i ) SEQUENCE DESCRIPTION: SEQ ID NO:70:

TTTTTGTGTG TGGGAAGTA  19

( 2 ) INFORMATION FOR SEQ ID NO:71:

( i ) SEQUENCE CHARACTERISTICS:
( A ) LENGTH: 21

(B) TYPE: nucleic acid
(C) STRANDEDNESS: single
(D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
    (A) ORGANISM: human (i x) FEATURE:
    (A) NAME/KEY: primer for exon 19 of human RB1 gene (x i) SEQUENCE DESCRIPTION: SEQ ID NO:71:

ATGACAAGCA GTTTTCCTAT T              21

(2) INFORMATION FOR SEQ ID NO:72:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (i x) FEATURE:
        (A) NAME/KEY: primer for exon 23 of human RB1 gene (x i) SEQUENCE DESCRIPTION: SEQ ID NO:72:

CCAGGGTAGG TCAAAAGTAT CC             22

(2) INFORMATION FOR SEQ ID NO:73:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (i x) FEATURE:
        (A) NAME/KEY: primer for exon 24 of human RB1 gene (x i) SEQUENCE DESCRIPTION: SEQ ID NO:73:

ATGTATTTAT GCTCATCTCT GC             22

(2) INFORMATION FOR SEQ ID NO:74:

(i) SEQUENCE CHARACTERISTICS:

( A ) LENGTH: 22
           ( B ) TYPE: nucleic acid
           ( C ) STRANDEDNESS: single
           ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
           ( A ) ORGANISM: human ( i x ) FEATURE:
           ( A ) NAME/KEY: primer for exon 26 of human RB1 gene ( x i ) SEQUENCE DESCRIPTION: SEQ ID NO:74:

TCGAAAGCAT CARAGTTACT GG                22

( 2 ) INFORMATION FOR SEQ ID NO:75:

( i ) SEQUENCE CHARACTERISTICS:
           ( A ) LENGTH: 22
           ( B ) TYPE: nucleic acid
           ( C ) STRANDEDNESS: single
           ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
           ( A ) ORGANISM: human ( i x ) FEATURE:
           ( A ) NAME/KEY: primer for promoter region of human RB1 gene ( x i ) SEQUENCE DESCRIPTION: SEQ ID NO:75:

ACAGTCACCC ACCAGACTCT TT                22

( 2 ) INFORMATION FOR SEQ ID NO:76:

( i ) SEQUENCE CHARACTERISTICS:
           ( A ) LENGTH: 19
           ( B ) TYPE: nucleic acid
           ( C ) STRANDEDNESS: single
           ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
           ( A ) ORGANISM: human ( i x ) FEATURE:
           ( A ) NAME/KEY: primer for exon 1 of human RB1 gene ( x i ) SEQUENCE DESCRIPTION: SEQ ID NO:76:

CGCCCGCCCT ACGCACACC                    19

( 2 ) INFORMATION FOR SEQ ID NO:77:

( i ) SEQUENCE CHARACTERISTICS:
    ( A ) LENGTH: 17
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 1 of human RB1 gene ( x i ) SEQUENCE DESCRIPTION: SEQ ID NO:77:

CGTGAGCGCG GGCGGAA    17

( 2 ) INFORMATION FOR SEQ ID NO:78:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 2 of human RB1 gene ( x i ) SEQUENCE DESCRIPTION: SEQ ID NO:78:

TAGTGATTTG AAGTTGTT    18

( 2 ) INFORMATION FOR SEQ ID NO:79:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 2 of human RB1 gene ( x i ) SEQUENCE DESCRIPTION: SEQ ID NO:79:

ATGTGCAAAC TATTGAAA    18

( 2 ) INFORMATION FOR SEQ ID NO:80:

( i ) SEQUENCE CHARACTERISTICS:
 ( A ) LENGTH: 22
 ( B ) TYPE: nucleic acid
 ( C ) STRANDEDNESS: single
 ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
 ( A ) ORGANISM: human ( i x ) FEATURE:
 ( A ) NAME/KEY: primer for exon 3 of human RB1 gene ( x i ) SEQUENCE DESCRIPTION: SEQ ID NO:80:

CTATTGAGAG GAAAATCCAG AA             22

( 2 ) INFORMATION FOR SEQ ID NO:81:

( i ) SEQUENCE CHARACTERISTICS:
  ( A ) LENGTH: 21
  ( B ) TYPE: nucleic acid
  ( C ) STRANDEDNESS: single
  ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
  ( A ) ORGANISM: human ( i x ) FEATURE:
  ( A ) NAME/KEY: primer for exon 3 of human RB1 gene ( x i ) SEQUENCE DESCRIPTION: SEQ ID NO:81:

TAACATAGTA GTATCCAGTG T             21

( 2 ) INFORMATION FOR SEQ ID NO:82:

( i ) SEQUENCE CHARACTERISTICS:
  ( A ) LENGTH: 18
  ( B ) TYPE: nucleic acid
  ( C ) STRANDEDNESS: single
  ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
  ( A ) ORGANISM: human ( i x ) FEATURE:
  ( A ) NAME/KEY: primer for exon 4 of human RB1 gene ( x i ) SEQUENCE DESCRIPTION: SEQ ID NO:82:

ATCAGAGTGA AACCCTAA             18

( 2 ) INFORMATION FOR SEQ ID NO:83:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 5 of human RB1 gene ( x i ) SEQUENCE DESCRIPTION: SEQ ID NO:83:

AGATGTTTGA GATTATTCCA        20

( 2 ) INFORMATION FOR SEQ ID NO:84:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 5 of human RB1 gene ( x i ) SEQUENCE DESCRIPTION: SEQ ID NO:84:

TAAATTACGA AAAAATGTTA        20

( 2 ) INFORMATION FOR SEQ ID NO:85:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 6 of human RB1 gene ( x i ) SEQUENCE DESCRIPTION: SEQ ID NO:85:

CAGAGAATGA GGGAGGAGTA        20

( 2 ) INFORMATION FOR SEQ ID NO:86:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 7 of human RB1 gene ( x i ) SEQUENCE DESCRIPTION: SEQ ID NO:86:

TGTCTTATCT TTCCTTCTAT          20

( 2 ) INFORMATION FOR SEQ ID NO:87:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 7 of human RB1 gene ( x i ) SEQUENCE DESCRIPTION: SEQ ID NO:87:

TGCGATTTTC TCTCATACAA          20

( 2 ) INFORMATION FOR SEQ ID NO:88:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 8 of human RB1 gene ( x i ) SEQUENCE DESCRIPTION: SEQ ID NO:88:

CATAACAAAA GAAGTAAAT          19

( 2 ) INFORMATION FOR SEQ ID NO:89:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 8 of human RB1 gene ( x i ) SEQUENCE DESCRIPTION: SEQ ID NO:89:

ATGTTACCAA GATTATTTT           19

( 2 ) INFORMATION FOR SEQ ID NO:90:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 9 of human RB1 gene ( x i ) SEQUENCE DESCRIPTION: SEQ ID NO:90:

TCCACAGTCT CAAAACATTA           20

( 2 ) INFORMATION FOR SEQ ID NO:91:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 10 of human RB1 gene ( x i ) SEQUENCE DESCRIPTION: SEQ ID NO:91:

TATCTAAAGC AAATCAATC                    19

( 2 ) INFORMATION FOR SEQ ID NO:92:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 11 of human RB1 gene ( x i ) SEQUENCE DESCRIPTION: SEQ ID NO:92:

AATCTGAAAC ACTATAAA                     18

( 2 ) INFORMATION FOR SEQ ID NO:93:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 12 of human RB1 gene ( x i ) SEQUENCE DESCRIPTION: SEQ ID NO:93:

TGTTAGATAG GAGATTAGT                    19

( 2 ) INFORMATION FOR SEQ ID NO:94:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 12 of human RB1 gene ( x i ) SEQUENCE DESCRIPTION: SEQ ID NO:94:

CCCTTCATTG CTTAACAC    18

( 2 ) INFORMATION FOR SEQ ID NO:95:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 13 of human RB1 gene ( x i ) SEQUENCE DESCRIPTION: SEQ ID NO:95:

TCTGATTAGA CAGTATCC    18

( 2 ) INFORMATION FOR SEQ ID NO:96:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 13 of human RB1 gene ( x i ) SEQUENCE DESCRIPTION: SEQ ID NO:96:

GAACTGGAAA GATGCTGC    18

( 2 ) INFORMATION FOR SEQ ID NO:97:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 14 of human RB1 gene ( x i ) SEQUENCE DESCRIPTION: SEQ ID NO:97:

TCTTGATGCC TTGACCTC 18

( 2 ) INFORMATION FOR SEQ ID NO:98:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exonS 15 AND 16 of human RB1 gene ( x i ) SEQUENCE DESCRIPTION: SEQ ID NO:98:

ATACTTACTT CTATAAAAAG 20

( 2 ) INFORMATION FOR SEQ ID NO:99:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exonS 15 AND 16 of human RB1 gene ( x i ) SEQUENCE DESCRIPTION: SEQ ID NO:99:

CCAAAGAAAC ACACCACATT 20

( 2 ) INFORMATION FOR SEQ ID NO:100:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 17 of human RB1 gene ( x i ) SEQUENCE DESCRIPTION: SEQ ID NO:100:

CTGATAATAA CTTCCAAAAA                20

( 2 ) INFORMATION FOR SEQ ID NO:101:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 18 of human RB1 gene ( x i ) SEQUENCE DESCRIPTION: SEQ ID NO:101:

TCCCTACAGT TTCTTTAT                18

( 2 ) INFORMATION FOR SEQ ID NO:102:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 18 of human RB1 gene ( x i ) SEQUENCE DESCRIPTION: SEQ ID NO:102:

TTTGATATGT ACCTGGGA                18

( 2 ) INFORMATION FOR SEQ ID NO:103:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:

( A ) NAME/KEY: primer for exon 19 of human RB1 gene ( x i ) SEQUENCE DESCRIPTION: SEQ ID NO:103:

GATGAGGAAA CTGAGACA                    18

( 2 ) INFORMATION FOR SEQ ID NO:104:

( i ) SEQUENCE CHARACTERISTICS:
                ( A ) LENGTH: 18
                ( B ) TYPE: nucleic acid
                ( C ) STRANDEDNESS: single
                ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
                ( A ) ORGANISM: human ( i x ) FEATURE:
                ( A ) NAME/KEY: primer for exon 19 of human RB1 gene ( x i ) SEQUENCE DESCRIPTION: SEQ ID NO:104:

GTGATTCTTA GCCAACTT                    18

( 2 ) INFORMATION FOR SEQ ID NO:105:

( i ) SEQUENCE CHARACTERISTICS:
                ( A ) LENGTH: 20
                ( B ) TYPE: nucleic acid
                ( C ) STRANDEDNESS: single
                ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
                ( A ) ORGANISM: human ( i x ) FEATURE:
                ( A ) NAME/KEY: primer for exon 20 of human RB1 gene ( x i ) SEQUENCE DESCRIPTION: SEQ ID NO:105:

AGTAGGGAGG AGAGAAGGTG                    20

( 2 ) INFORMATION FOR SEQ ID NO:106:

( i ) SEQUENCE CHARACTERISTICS:
                ( A ) LENGTH: 20
                ( B ) TYPE: nucleic acid
                ( C ) STRANDEDNESS: single
                ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
                ( A ) ORGANISM: human ( i x ) FEATURE:
  ( A ) NAME/KEY: primer for exon 20 of human RB1 gene ( x i ) SEQUENCE DESCRIPTION: SEQ ID NO:106:

CAAAATGAAC AGTAAAAATG            20

( 2 ) INFORMATION FOR SEQ ID NO:107:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 21 of human RB1 gene ( x i ) SEQUENCE DESCRIPTION: SEQ ID NO:107:

CTATGTTATG TTATGGAT            18

( 2 ) INFORMATION FOR SEQ ID NO:108:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 21 of human RB1 gene ( x i ) SEQUENCE DESCRIPTION: SEQ ID NO:108:

AAAGAAAGAA AATGGTAT            18

( 2 ) INFORMATION FOR SEQ ID NO:109:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 22 of human RB1 gene ( x i ) SEQUENCE DESCRIPTION: SEQ ID NO:109:

TGGTGGACCC ATTACATT                18

( 2 ) INFORMATION FOR SEQ ID NO:110:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 22 of human RB1 gene ( x i ) SEQUENCE DESCRIPTION: SEQ ID NO:110:

ACCAGTCAAA AAGTATTA                18

( 2 ) INFORMATION FOR SEQ ID NO:111:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 23 of human RB1 gene ( x i ) SEQUENCE DESCRIPTION: SEQ ID NO:111:

TCTCATTCTT TACTACTT                18

( 2 ) INFORMATION FOR SEQ ID NO:112:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:

( A ) ORGANISM: human ( i x ) FEATURE:
    ( A ) NAME/KEY: primer for exon 23 of human RB1 gene ( x i ) SEQUENCE DESCRIPTION: SEQ ID NO:112:

TTGGAAAAAT CTAATGTA　　　　　　18

( 2 ) INFORMATION FOR SEQ ID NO:113:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 24 of human RB1 gene ( x i ) SEQUENCE DESCRIPTION: SEQ ID NO:113:

CTTTTATACT TACAATGC　　　　　　18

( 2 ) INFORMATION FOR SEQ ID NO:114:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 24 of human RB1 gene ( x i ) SEQUENCE DESCRIPTION: SEQ ID NO:114:

TATGGTTTTT TATTACTA　　　　　　18

( 2 ) INFORMATION FOR SEQ ID NO:115:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal (vi) ORIGINAL SOURCE:
  (A) ORGANISM: human (ix) FEATURE:
  (A) NAME/KEY: primer for exon 25 of human RB1 gene (xi) SEQUENCE DESCRIPTION: SEQ ID NO:115:

ATGACCATCT CAGCTACT    18

(2) INFORMATION FOR SEQ ID NO:116:

(i) SEQUENCE CHARACTERISTICS:
    (A) LENGTH: 19
    (B) TYPE: nucleic acid
    (C) STRANDEDNESS: single
    (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
    (A) ORGANISM: human (ix) FEATURE:
    (A) NAME/KEY: primer for exon 25 of human RB1 gene (xi) SEQUENCE DESCRIPTION: SEQ ID NO:116:

TTGCTAACTA TGAAACACT    19

(2) INFORMATION FOR SEQ ID NO:117:

(i) SEQUENCE CHARACTERISTICS:
    (A) LENGTH: 18
    (B) TYPE: nucleic acid
    (C) STRANDEDNESS: single
    (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
    (A) ORGANISM: human (ix) FEATURE:
    (A) NAME/KEY: primer for exon 26 of human RB1 gene (xi) SEQUENCE DESCRIPTION: SEQ ID NO:117:

ATTGTTTATT TCGTTTAC    18

(2) INFORMATION FOR SEQ ID NO:118:

(i) SEQUENCE CHARACTERISTICS:
    (A) LENGTH: 18
    (B) TYPE: nucleic acid
    (C) STRANDEDNESS: single
    (D) TOPOLOGY: linear (ii) MOLECULE TYPE: genomic DNA (iii) HYPOTHETICAL: no (iv) ANTI-SENSE: no (v) FRAGMENT TYPE: internal (v i) ORIGINAL SOURCE:
    (A) ORGANISM: human (i x) FEATURE:
    (A) NAME/KEY: primer for exon 26 of human RB1 gene (x i) SEQUENCE DESCRIPTION: SEQ ID NO:118:

ATTTGAGTTT TCCATTTA                18

(2) INFORMATION FOR SEQ ID NO:119:

(i) SEQUENCE CHARACTERISTICS:
        (A) LENGTH: 19
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (i x) FEATURE:
        (A) NAME/KEY: primer for exon 27 of human RB1 gene (x i) SEQUENCE DESCRIPTION: SEQ ID NO:119:

CTTAGGAATC ACCCAAACA               19

(2) INFORMATION FOR SEQ ID NO:120:

(i) SEQUENCE CHARACTERISTICS:
        (A) LENGTH: 19
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (v i) ORIGINAL SOURCE:
        (A) ORGANISM: human (i x) FEATURE:
        (A) NAME/KEY: primer for exon 27 of human RB1 gene (x i) SEQUENCE DESCRIPTION: SEQ ID NO:120:

AGTACCATCA ATGCTGTTA               19

(2) INFORMATION FOR SEQ ID NO:121:

(i) SEQUENCE CHARACTERISTICS:
        (A) LENGTH: 19
        (B) TYPE: nucleic acid
        (C) STRANDEDNESS: single
        (D) TOPOLOGY: linear (i i) MOLECULE TYPE: genomic DNA (i i i) HYPOTHETICAL: no (i v) ANTI-SENSE: no (v) FRAGMENT TYPE: internal (vi) ORIGINAL SOURCE:
            (A) ORGANISM: human (ix) FEATURE:
            (A) NAME/KEY: primer for promoter region of human RB1 gene (xi) SEQUENCE DESCRIPTION: SEQ ID NO:121:

CTGAGAAAAA CCGGACGCG                    19

(2) INFORMATION FOR SEQ ID NO:122:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 4 of human RB1 gene (xi) SEQUENCE DESCRIPTION: SEQ ID NO:122:

ATATAGTAGT GATTTGATGT                   20

(2) INFORMATION FOR SEQ ID NO:123:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 4 of human RB1 gene (xi) SEQUENCE DESCRIPTION: SEQ ID NO:123:

ATGACATAAA AAATCAGAGT                   20

METHOD, REAGENTS AND KIT FOR DIAGNOSIS AND TARGETED SCREENING FOR RETINOBLASTOMA

BACKGROUND OF THE INVENTION

This application relates to a method, reagents and kits for diagnosis and targeted screening for retinoblastoma.

Retinoblastoma is a form of cancer affecting the eyes of young children. It results from mutations in the RB1 gene that lead to the loss of functional RB protein in the retinoblasts of the fetal and juvenile eye. Because the RB protein is involved in the control mechanism for proteins or peptides that promote cell division, cells lacking in functional RB protein undergo unregulated division, leading to the formation of a tumor within the eye.

The impact of the tumor within the eye depends in large part on the size of the tumor when detected. If the tumor is very large, it may be necessary to remove the eye completely. Smaller tumors may be treated with techniques such as photocoagulation, cryotherapy or radiation, making it possible to save visual function, although treatment with radiation, which is necessary in more advanced cases, increases the risk of subsequent tumor formation. It is thus very important to the prognosis of the patient to detect retinoblastoma early on. Unfortunately, retinoblastoma is not accompanied by any readily identified early symptoms, nor is there a blood test which can be routinely administered to screen for the disease. For this reason, most early detection of retinoblastoma occurs only when one member of a family has already been diagnosed as having retinoblastoma.

The accepted procedure which is currently followed after a diagnosis of retinoblastoma in one child of a family is to carefully monitor that child's siblings and first cousins during the period of significant risk, i.e., generally through about age seven. This monitoring, which involves frequent doctor visits, and frequently includes examination under anesthesia, is very costly. It would therefore be desirable to have a mechanism for determining the genetic basis for any given child's tumors, to be more fully able to assess which of the child's siblings and other relatives are actually at risk, and to permit genetic testing of potentially-at-risk individuals to limit monitoring to those actually at risk.

Mechanisms for genetic testing for retinoblastoma have been previously proposed. For example, RNase protection of the mRNA of retinoblastoma is able to detect about 70% of mutations to the RB1 gene, but is dependent on the existence of retinoblastoma tumor mRNA. Dunn et al., *Science* 241: 1797 (1988); Dunn et al., *Mol. Cell. Biol.* 9:4594 (1989). Complete sequencing of each exon might also be performed as described by Yandell et al., *N. Engl. J. Med.* 321: 1689 (1989), but the cost associated with this approach using existing technology is prohibitive. Because of this cost factor, it was previously suggested that the exons of the RB1 molecule could be screened using mobility differences as described in Orita et al., *Proc. Nat'l Acad. Sci. U.S.A.* 86: 2766 (1989) so that only those believed to contain a mutation would be sequenced. Gallie, B. L., "The Misadventures of RB1" in *Causes and Consequences of Chromosomal Aberrations*, pp 429–446, CRC Press (1993).

Unfortunately, despite its early promise, the use of exon screening based on mobility differences followed by selective exon sequencing has proven unreliable for providing diagnostic and targeted screening results concerning retinoblastoma. Thus, there is still no cost effective and reliable test which can be performed on individuals diagnosed with retinoblastoma and their juvenile relations to eliminate unneeded physical examinations. It is an object of the present invention to provide such a test.

SUMMARY OF THE INVENTION

In accordance with the present invention, reliable and cost effective testing for mutations in the RB1 gene can be achieved by (a) quantitatively amplifying exons of the sample RB1 gene using primers complementary to intron regions flanking each exon;

(b) determining the lengths or quantity of the amplification products for each exon amplified and comparing that length or quantity to the length or quantity of amplification products obtained when a wild-type RB1 gene is amplified using the same primers, whereby differences in length between an amplified sample exon and the corresponding amplified wild-type exon reflect the occurrence of an insertion or deletion mutation in the sample RB1 gene; and (c) determining the nucleic acid sequence of each exon found to contain an insertion or deletion mutation, or of all exons in the event no insertion or deletion mutations are identified. Preferably, the amplification of the exons is multiplexed so that more than one exon is amplified in a single vessel using sets of primers which provide gene fragments of distinctive lengths when used to amplify a normal RB1 gene.

The information obtained in the test is used to generate a report which is used to provide appropriate genetic counseling to the family of individuals diagnosed with retinoblastoma. The generation of such reports, which may be in the form of a printed report, an electronic communication, such as a facsimile or electronic mail (e-mail) transmission, or a posting of a data entry in a computer record relating to the patient, is a further aspect of the present invention.

In order to practice the method of the present invention, it was necessary to develop a multitude of primers for amplification. These primers, taken individually or as part of kits for detection of RB1 mutations represent a further aspect of the present invention. Particularly preferred primers constitute sets that are compatible for coamplification and that produce amplified gene fragments of distinctive length from primers for other exons within the same set.

DETAILED DESCRIPTION OF THE INVENTION

The present invention relates to a method for the identification of mutations in the RB1 gene, method for generating reports and providing family counseling to relatives of patients with RB1 mutations, and to oligonucleotide primers and kits useful in practicing these methods.

The method for identification of mutations in the RB1 gene is based upon a hierarchical approach in which a sample derived from a patient diagnosed with retinoblastoma is first tested with a test of moderate accuracy but high specificity, that is a test which detects about 50% of all mutations (i.e., about 50% false negatives), but essentially never gives a false positive reading. A sample which exhibits a negative result is thereafter subjected to a more costly, but more accurate test to determine if a mutation is present. By eliminating this test from over half of the samples, however, the average cost of the test goes down without sacrificing analytical performance. This hierarchical approach is an example of a more general method which is described in concurrently filed U.S. patent application Ser. No. 08/271, 946, which is incorporated herein by reference.

Figure 1:
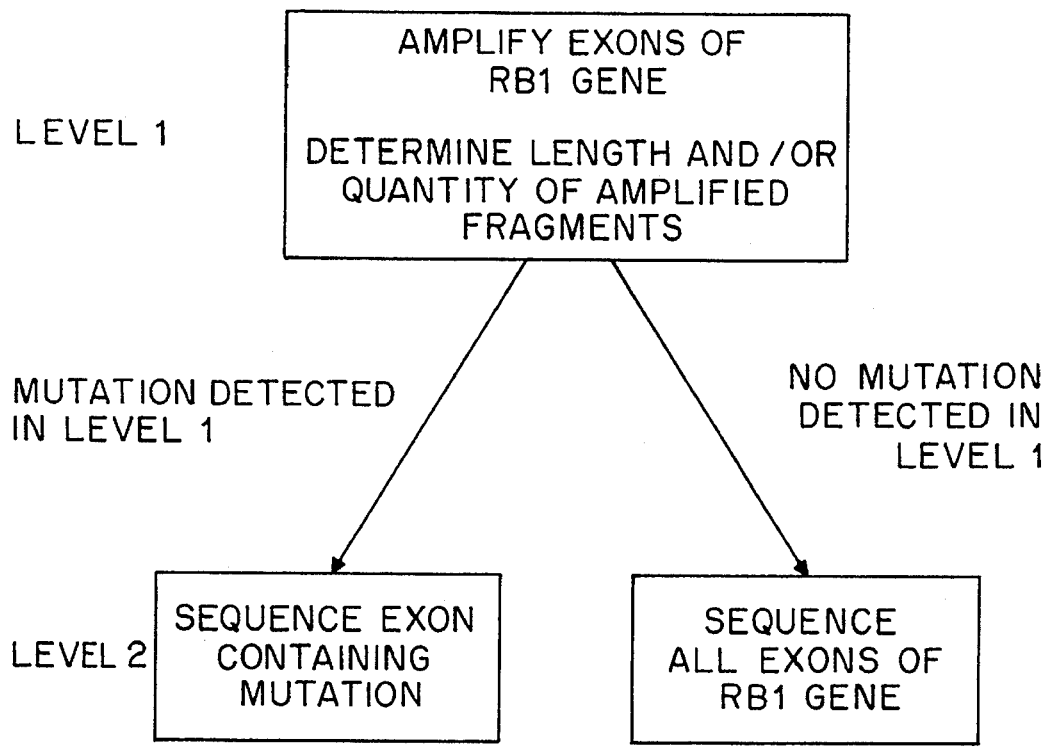
FIG. 1 shows a schematic representation of the hierarchical analysis method for identification of mutations in the RB1 gene in accordance with the present invention.

In the case of testing for mutations in the RB1 gene, the hierarchy preferably consists of two levels. Level 1, as shown in FIG. 1, involves a test performed on all patient samples. In this test, one or more exons of the RB1 gene are individually quantitatively amplified and the lengths and/or quantity of the amplified fragments are determined. If there is a variance between the length of any amplified exon, and the normal length of that exon, this is an indication of an insertion or deletion mutation in that exon. The quantity of amplified material from amplification of a sample exon may also reflect the loss of genetic material. In particular, by comparing the quantity of amplified materials produced to standards amplified from a null allele (0 copies of RB1), a hemizygous standard (1 copy of RB1), a wild type standard (2 copies of RB1) and a trisomy standard (3 copies of RB1) the nature of a mutation may be further investigated.

The number of exons tested in Level 1 of the hierarchy is a matter of choice for the user. For example, it has been observed that disease-associated mutations in the RB1 gene rarely occur in exons 5, 25, 26 and 27. It may therefore be desirable to test these exons last, after testing other exons to see if a mutation sufficient to cause the disease is detected, before incurring the expense to test these less likely exons. In testing these other exons, the user may choose to test them one at a time, or in one multiplexing group at a time. Alternatively, the user may choose to test all exons simultaneously at the first level of the hierarchy.

When a mutation is detected in level one of the hierarchy, it is not necessary to perform additional tests on the patient sample to complete the identification process. Preferably, however, the sequence of the mutated exon will be determined as part of the second level of the hierarchy to confirm that the mutation detected can in fact be a cause of the observed disease.

Figure 2:
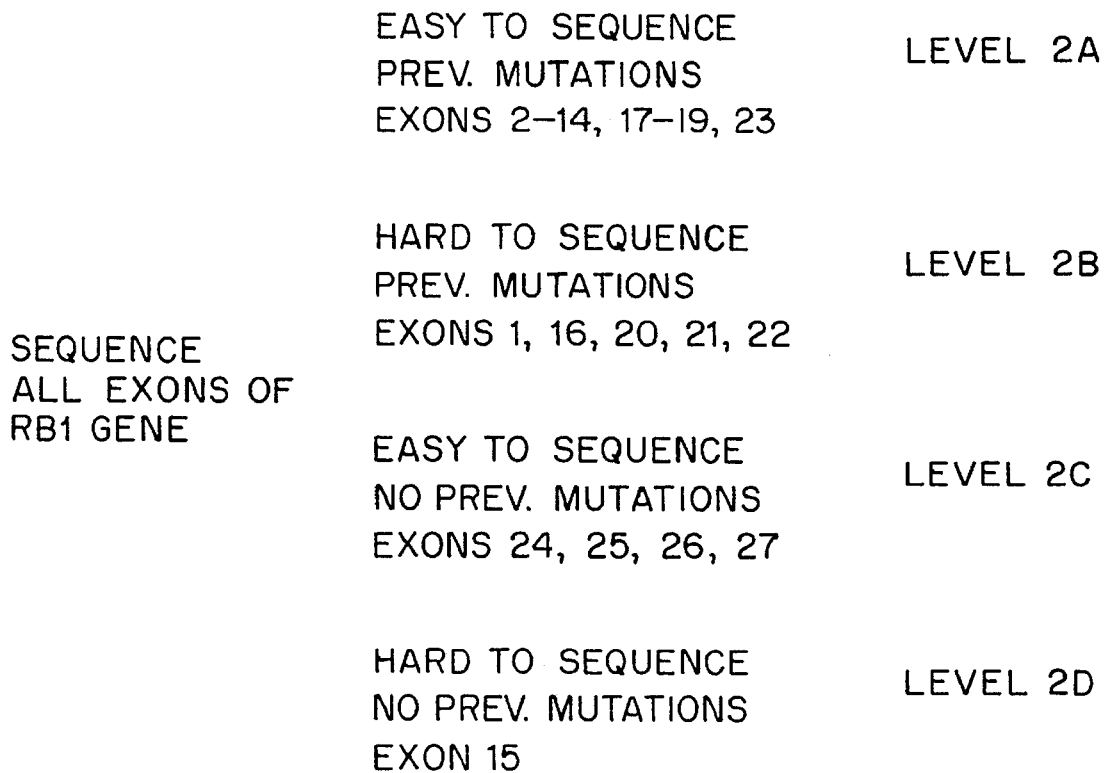
FIG. 2 shows a sub-hierarchy useful in the sequencing step of the method of the invention.

If no mutation is detected in the first level of testing, the second level of tests is performed. This involves determining the sequence of the exons to locate the mutation. Sequencing is expensive, however, and so it may be desirable to use a sub-hierarchy within this level of testing to reduce the likelihood of having to sequence all of the exons. In this case, a suitable sub-hierarchy is shown in FIG. 2. In accordance with this sub-hierarchy, the first exons sequenced (Level 2A) are those which are easy to sequence and which have been the site of other disease-associated associated mutations. Next, if no mutation which could result in retinoblastoma is found, exons are sequenced which are hard to sequence and which have been the site of other disease-associated mutations (Level 2B). The third level of the sub-hierarchy includes exons which are easy to sequence but which have never been shown to contain a disease-associated mutation (Level 2C). Finally, exons are sequenced which are hard to sequence but which have never been shown to contain a disease-associated mutation (Level 2D).

The primers used to amplify the sample DNA for the first test in the hierarchy are oligonucleotides of defined sequence selected to hybridize selectively with particular portions of the RB1 gene. Each primer has bound to it a detectable label. A preferred example of such a label is fluorescein, which is a standard label used in nucleic acid sequencing systems using laser light as a detection system. Other detectable labels can also be employed, however, including other fluorophores, radio-labels, chemical couplers such as biotin which can be detected with streptavidin-linked enzymes, and epitope tags such as digoxigenin detected using antibodies available from Boehringer-Mannheim.

While considerable variation is possible in the sequence of the primers used in amplifying the exons during the first step in the method of the present invention, the primers used in amplification and the conditions of the amplification are preferably optimized for use in the present invention. Looking first at the primers used, it will be understood that in order to avoid the possibility of false positive results the primer pair, i.e., the combination of the 5'-primer and the 3'-primer for any given exon must be unique to the RB1 gene so that only the RB1 gene will be amplified. This means that the primer sequences will be generally somewhat longer than the minimum which can be used as an amplification primer. Preferred primers are from 18 to 23 nucleotides in length, without internal homology or primer-primer homology. It is also desirable for the primers to form more stable duplexes with the target DNA at the primer's 5'-ends than at their 3'-ends, because this leads to less false priming. Stability can be approximated by GC content, since GC base pairs are more stable than AT pairs, or by nearest neighbor thermodynamic parameters. Breslauer et al., "Predicting DNA duplex stability from base sequence", *Proc. Nat'l Acad. Sci. USA* 83: 3746–3750 (1986). In addition, to ensure complete amplification of each exon, the two primers of a pair are preferably selected to hybridize in the introns immediately flanking the exon to be amplified using the primer pair.

Additional factors apply to the selection of primers for multiplexed amplification of exons. These factors are discussed in Rylchik, W., Selection of Primers for Polymerase Chain Reaction", in *Methods in Molecular Biology, Vol. 15: PCR Protocols: Current Methods and Applications*, White, B. A. ed., Humana Press, Totowa, N.J., 1993. Briefly, applying these factors, primer pairs are selected by position, similarity of melting temperature, internal stability, absence of internal homology or homology to each other, i.e., they won't stick to each other or to themselves, and the 3'-end will not form a stable hairpin loop back on itself.

Thus, in the present case, the goal is to have sets of primer pairs with approximately the same thermal profile, so that they can be effectively coamplified together. This goal can be achieved by having groups of primer pairs with approximately the same length and the same G/C content. In addition, it is preferred that the length of the gene region between the primer binding sites on a normal RB1 gene differ for each exon to be multiplexed as a group. Differences of only one base in length are sufficient, provided a high resolution gel capable of resolving one base differences is used in analyzing the amplification products. However, greater differences in length are preferred.

To evaluate compatibility of primers for use in coamplification, it is desirable to determine the predicted melting temperature for each primer. This can be accomplished in several ways. For example, the melting temperature, Tm can be calculated using either of the following equations:

$$Tm(°C) = 8.15 + 16.6 \times \log [Na] + 0.41 \times (\% \, GC) - 675/\text{length}$$

where [Na] is the concentration of sodium ions, and the % GC is in number percent, or $$Tm(°C) = 2 \times (A+T) + 4 \times (G+C)$$

where A, T, G, and C represent the number of adenosine, thymidine, guanosine and cytosine residues in the primer. In general, primers for coamplification should be selected to have predicted melting temperatures differing by less than 4° C.

The process of selecting primers for use in the invention can be illustrated with reference to exons 4 and 6 of the RB1 gene. Two primer pairs have been identified for exon 4 and one primer pair has been identified for exon 6. Primer 4×5'-A is a 20-mer having the sequence ATATAGTAGT GATTTGATGT [Seq.ID No.: 122] which is homologous to a region in the intron immediately adjacent to the 5'-end of exon 4 of the RB1 gene. This region starts 122 bases from the 5'-end of the exon and extends to the base which is 103 bases from the exon. The primer has a predicted melting temperature of 50° C.

Primer 4×3'-A is a 20-mer having the sequence

ATGACATAAA AAATCAGAGT [Seq.ID No.: 123] which is homologous to a region in the intron adjacent to the 3'-end of exon 4 of the RB1 gene. This region starts 28 bases from the 3'-end of the exon and extends to the base which is 47 bases from the exon. This primer also has a melting temperature of 50° C.

Primer 6×5' is a 22-mer having the sequence

CACAAAAAGA AACACCCAAA AG [Seq.ID No.: 61] which is homologous to a region in the intron adjacent to the 5'-end of exon 6 of the RB1 gene. This region starts 72 bases from the 5'-end of the exon and extends to the base which is 93 bases from the exon. The primer has a predicted melting temperature of 62° C.

Primer 6×3' is a 22-mer having the sequence

TAATAAGCCA AGCAGAGAAT GA [Seq.ID No.: 26] which is homologous to a region of the intron adjacent to the 3'-end of exon 6 of the RB1 gene. This region starts 107 bases from the 3'-end of the exon and extends to the base which is 128 bases from the exon. The primer has a predicted melting temperature of 60° C.

These two primer pairs are effective for the amplification of exons 4 and 6 individually. They are not suited for use together in a multiplexed amplification, however, because the melting temperatures of the two pairs are too different. Furthermore, both of these primer pairs produce an amplification product which is 289 bases in length. Thus, the two primer pairs cannot be used with a common detectable label in a multiplexed reaction.

In order to amplify exon 4 and exon 6 in a single reaction, it is necessary to identify a different primer pair for one of the two exons which is compatible with the primer pair for the other exon. In this case, a suitable replacement is the primer pair identified by the inevntors as 4×5'-B and 4×3'-B.

The primer 4×5'-B is a 22-mer having the sequence

AGTAGTGATT TGATGTAGAG CT [Seq.ID No.: 59] which is homologous to the region in the intron adjacent to the 5'-end of exon 4 that starts 98 bases from the 5'-end of the exon and extends to the base which is 119 bases from the exon. This primer has a melting temperature of 60° C. The primer 4×3'-B is a 22-mer having the sequence ATAAAAAATC AGAGTGTAAC CC [Seq.ID No.: 40] which is homologous to the region in the intron adjacent to the 3'-end of exon 4 starting 21 bases from the 5'-end of the exon and extends to the base which is 42 bases from the exon. This primer has a melting temperature of 58° C. Thus, these primers have melting temperatures which are much closer to the melting temperature of the exon 6 primers. Moreover, the amplification product has a length of 280 bases, which is 9 bases different from the amplification product of the exon 6 primers.

In addition to the selection of suitable primers, best results in the fragment length analysis are obtained if the amplification reaction is carried out for a limited number of amplification cycles. It will be understood, that the more cycles of amplification are carried out, the more of the desired product will be made and thus the easier its detection will be. It should also be recognized, however, that during the initial cycles (generally the first 20–25 cycles), the amount of DNA of the desired sequence doubles in each cycle, while thereafter the yield of desired product per cycle drops off. For maximum effectiveness in the method of the present invention, the amplification of the exons in the patient sample should be carried out only for a number of cycles during which doubling of DNA is still being achieved. Such amplification is referred to in the specification and claims hereof as "quantitative" amplification.

After amplification of the exons of RB1 gene, the amplification products are analyzed electrophoretically using a sequencing gel. Preferred gels will have a resolution of one base pair, so that one base deletions or insertions, which are relatively common in cases of retinoblastoma, can be identified. A suitable gel is a polyacrylamide gel of the type recommended for use with the Pharmacia A.L.F. Sequencer.

The type of detector system used to analyze the gel depends on the type of label employed on the amplification primers. For example, in the case of radio-labeled primers, the gel might be analyzed by autoradiography. The preferred labels, however, are fluorophores which are detected using photodiodes, photomultipliers or other light sensitive devices.

Figure 3:
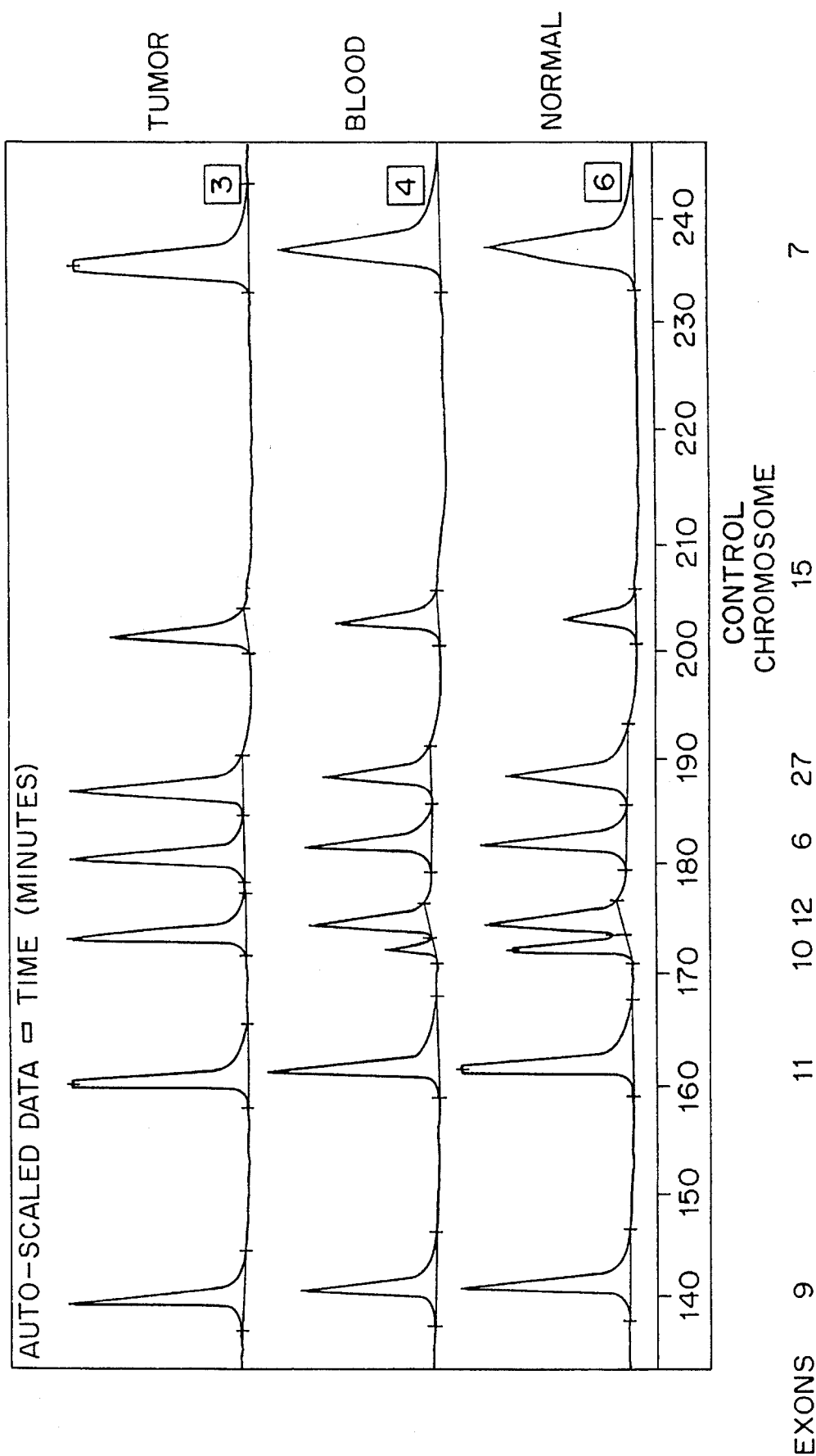
FIG. 3 shows a sample output of a Pharmacia A.L.F. Sequencer using fluorescein-labelled primers when exons 6, 9, 10, 11, 12 and 27 were coamplified.

FIG. 3 shows a sample output of a Pharmacia A.L.F. Sequencer using fluorescein-labelled primers. Each peak in the output corresponds to a single-stranded fluorescein-labeled amplified DNA product from a PCR reaction migrating in the gel. Each exon of the RB1 gene and a control exon from a gene on chromosome 15 unrelated to RB1 migrate at a different rate. By comparison of the peaks from the patient samples to those of the wild type, it can be determined that a mutation exists, in this case the complete deletion of exon 10 from one allele, or the deletion of part of an exon and one of the priming sites. In a sample from the patient's tumor tissue, the mutation is homozygous (no exon 10), while in the blood of this patient, the exon 10 peak is reduced by 50% indicating that this patient carries the mutation in his or her somatic tissue, and therefore probably in their germline. The deletion of exon 10 leads to a severely truncated RB1 protein lacking many of the regions required for proper function, therefore it can be safely assumed that this is the disease causing mutation.

The second level of the hierarchy calls for the sequencing of one or more exons of the RB1 gene. Preferably, this sequencing process is performed on amplified DNA. The primers used in the pre-sequencing amplification can have the same sequence as those used in the first level of the test hierarchy, or they may be different. In either case, however, it is preferred that instead of the detectable labels used on the primers in the first level amplification, during pre-sequencing amplification one of the primers of each pair will be modified to facilitate recovery. For example, one primer of each pair may be biotinylated so that it can be recovered by binding to a streptavidin-coated support.

Once the mutation responsible for the retinoblastoma has been identified, additional tests are performed on family members to provide a basis for appropriate counseling and monitoring. Again, the most cost effective approach is hierarchical.

Figure 4:
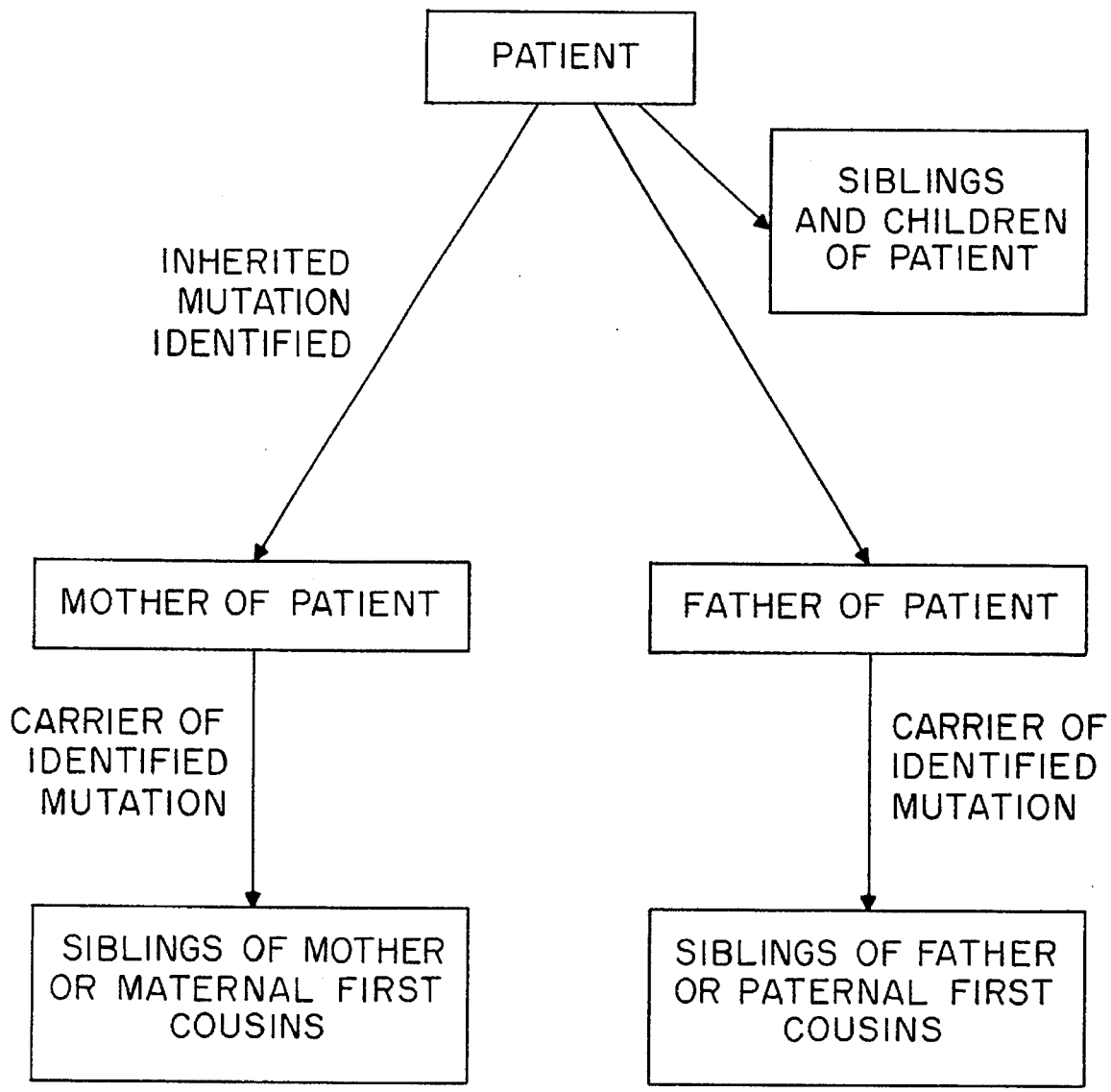
FIG. 4 shows a hierarchy for testing of family members of a patient after identification of the disease-associated mutation.

As shown in FIG. 4, an appropriate first step is the testing of the diagnosed child's parents and siblings. The test in this case involves amplification of the exon identified as having the disease-associated mutation using the level one primers. The amplified exon is then analyzed to determine if the same mutation is present. This may involve evaluation of the length and/or quantity of the amplification fragment, or sequencing, or both. If either parent is found to be a carrier of the disease-associated mutation, siblings of that parent should be tested to determine if they too carry the mutation. If they do, then their children should be tested. If they do not, then no testing of these first cousins of the diagnosed patient is necessary. If neither parent of the diagnosed patient is found to be a carrier of the disease-associated mutation, yet the mutation was detected in both blood and tumor tissue of the patient, then the mutation presumably arose through mosaicism, or during early development of the patient. In this case, all siblings of the patient should be tested, but other family members need not.

EXAMPLE 1

A blood sample is received from a patient diagnosed as suffering from retinoblastoma. Genomic DNA is prepared from the samples using a Qiagen QIAamp Kit according to the accompanying directions. Briefly, an aliquot of the sample, or a lymphocyte-containing fraction thereof, is combined with Proteinase K, mixed, and allowed to incubate to lyse the cells. Ethanol is added and the lysate is transferred to a QIAamp spin column from which DNA is recovered after several washings.

The genomic DNA is next amplified in five sets using multiplexing primers. Each 50 µl multiplexed PCR reaction contains 0.5 µg genomic DNA, 150 ng of each primer, 3.6 mM each dNTP, 42.5 µg Bovine Serum Albumin, 5 units Taq polymerase in a buffer containing 10% DMSO, 16 mM $(NH_4)_2SO_4$, 6.7 mM $MgCl_2$, 6.8 µM EDTA (pH 8.0) and 1 mM β-mercaptoethanol. The reaction mixture was initially incubated at 94° C. for 5 minutes and then subjected to an appropriate number of cycles of PCR in a Perkin-Elmer/Cetus thermocycler as follows:

denaturation 94° C., 30 seconds annealing 53° C. or 55° C., 30 seconds extension 72° C., 4 minutes - final extension 7 minutes.

In the first set, exons 2, 3, 5, 13 and 25 are amplified, together with a control sequence which is a DNA segment from chromosome 15, unrelated to RB1, for 18 cycles. The primers, one of each pair being labeled with fluorescein at the 5'-end, are

| exon | 5'-primer | 3'-primer |
|---|---|---|
| 2 | ACTGTGTGGT ATCCTTATTT TG [seq 1] | ATAGTGATTT GAAGTTGGTT TTA [seq 2] |
| 3 | ATACAGTTTT AACATAGTAT CCA [seq 3] | AAGTCTATTG AGAGGAAAAT CC [seq 4] |
| 5 | CTACTATGAC TTCTAAATTA CG [seq 5] | TCAAGATGTT TGAGATTATT CC [seq 6] |
| 13 | TGCTTATGTT CAGTAGTTGT G [seq 7] | TAATGGGGTG GGAGGTAGTT T [seq 8] |
| 25 | TCAAACTATA ACTTGAGGTT GC [seq 9] | AAAGAAATTG GTATAAGCCA GG [seq 10] |
| con | CTCACCCGCA CCTAAGTTT [seq 11] | CCAGGATGAG AGCGGATGGC A [seq 12] |

These primers result in amplified products with normal fragment lengths of 410, 262, 170, 461 and 316 base pairs, respectively. The control sequence produces a fragment having a length of 325 base pairs.

In the second set, exons 1, 8, 18, 21, 22, and 23 are amplified, together with the same control sequence, for 18 cycles. The primers, one of each pair of which is labeled with fluorescein, are

| exon | 5'-primer | 3'-primer |
|---|---|---|
| 1 | GCCCCAGTTC CCCACAGAC [seq 13] | ACCCCTCGCC CAAGAACCC [seq 14] |
| 8 | TCTAATGAAA CCTAATAAGT A [seq 15] | TGCTCATAAC AAAAGAAGTA A [seq 16] |
| 18 | TTTTTGTGTG TGGGAAGTAC A [seq 17] | ATTCTATTCC CTACAGTTTC TT [seq 18] |
| 21 | GGCTAAAAGA AAGAAAATGG [seq 19] | TTACCTATGT TATGTTATGG [seq 20] |
| 22 | TATGTGCTTC TTACCAGTCA AA [seq 21] | GGAGTCATTT TTGTTGGTGT TG [seq 22] |
| 23 | AATCTAATGT AATGGGTCCA CC [seq 23] | ATCAAAATAA TCCCCCTCTC AT [seq 24] |

These primers result in amplified products with normal fragment lengths of 591, 366, 418, 251, 496 and 283 base pairs, respectively.

In the third set, exons 6, 7, 9, 10, 11, 12 and 27 are amplified, together with the same control sequence, for 20 cycles. The primers, one of each pair being labeled with fluorescein, are

| exon | 5'-primer | 3'-primer |
|---|---|---|
| 6 | AAAGAAACAC CCAAAAGATA [seq 25] | TAATAAGCCA AGCAGAGAAT GA [seq 26] |
| 7 | TTATGGATAT ACTCTACCCT GC [seq 27] | CCTCCATTTG TTGTATTTTG AC [seq 28] |
| 9 | TCAAGAGTCA AGAGATTAGA [seq 29] | ATTATCCTCC CTCCACAGTC TC [seq 30] |
| 10 | GTGCTGAGAG ATGTAATGA [seq 31] | TATCTAAAGC AAATCAATC [seq 32] |
| 11 | TGAGACAACA GAAGCATTAT [seq 33] | TGAACAAATC TGAAACACTA T [seq 34] |
| 12 | CTCCCTTCAT TGCTTAACAC AT [seq 35] | AAAAGCAAGA AAAGATTATG G [seq 36] |
| 27 | ACTTACCCAG TACCATCAAT GC [seq 37] | TCAAGTGGCT TAGGAATCAC CC [seq 38] |

These primers result in amplified products with normal fragment lengths of 283, 423, 205, 264, 244, 270 and 297 base pairs, respectively.

In the fourth set, exons 4, 14, 20, 24 and 26 are amplified, together with the same control sequence, for 18 cycles. The primers, one of each pair being labeled with fluorescein, are

| exon | 5'-primer | 3'-primer |
|---|---|---|
| 4 | TTGAAAACGA AATAACAC [seq 39] | ATAAAAAATC AGAGTGTAAC CC [seq 40] |
| 14 | GTGATTTTCT AAAATAGCAG GC [seq 41] | CCAGGATGAT CTTGATGCC [seq 42] |
| 20 | GAAAAGAGTG GTAGAAAAGA GG [seq 43] | TAACAAGTAA GTAGGGAGGA GA [seq 44] |
| 24 | GTATTTATGC TCATCTCTGC [seq 45] | GTGTTTGAAT AACTGCATTT GG [seq 46] |
| 26 | CGAAAGCATC ATAGTTACTG G [seq 47] | ATATAACGAA AAGACTTCTT GC [seq 48] |

These primers result in amplified products with normal fragment lengths of 228, 227, 343, 206, and 203 base pairs, respectively.

In the fifth set, exons 15 and 16 are amplified together, along with exons 17, 19, the RB1 promoter region and the same control sequence, for 20 cycles. The primers, one of each pair being labeled with fluorescein, are

| exon | 5'-primer | 3'-primer |
|---|---|---|
| 15, 16 | CAATGCTGAC ACAAATAAGG TT [seq 49] | CCCCCGACCA AAGAAACACA [seq 50] |
| 17 | ACCTTTCTAC TGTTTTCTTT GT [seq 51] | AAACACCTCT CACTAACAAT [seq 52] |
| 19 | TGTATAATCT GTGATTCTTA GC [seq 53] | GCAACATTAT CATTTCCATT TT [seq 54] |
| PROM | CCCACCAGAC TCTTTGTA [seq 55] | ACGTCCCCTG AGAAAAACCG GA [seq 56] |

These primers result in amplified products with normal fragment lengths of 335, 371, 363, and 316 base pairs, respectively.

After amplification, the products from each amplification reaction are denatured and loaded onto a polyacrylamide sequencing gel in a Pharmacia A.L.F. automated sequencer. The single-stranded amplification products migrate through the gel at a rate determined by their length, and are detected using the fluorescence of the fluorescein label which was attached to the primers.

EXAMPLE 2

FIG. 3 shows the peaks detected in the third amplification group (exons 6, 9, 10, 11, 12 and 27 and the control exon) when samples of a diagnosed individual's blood and tumor material were treated as described in Example 1 and compared to a normal sample. The peak associated with exon 10 is completely missing in the tumor sample, and is present at only half intensity in the blood sample.

EXAMPLE 3

Blood samples were obtained from a juvenile female patient diagnosed with bilateral retinoblastoma, the patient's brother, biological parents, two maternal aunts and both maternal grandparents. The samples were evaluated in accordance with the procedure outlined in Example 1. Based on this test, the patient was found to be homozygous for a one-base pair deletion in exon 19 of the RB1 gene. The patient's mother was found to be heterozygous for the same mutation. No other family member tested had any detected abnormality in the RB1 gene.

Exon 19 from the patient was subsequently sequenced to confirm the presence of a mutation which would lead to retinoblastoma. Sequencing was performed by selectively amplifying exon 19 using the following primers:

5'-primer

ATGACAAGCA GTTTTCCTAT TA [Seq.ID No.: 89]

3'-primer

GCAACATTAT CATTTCCATT TT [Seq.ID No.: 90]

The 5'-primer was biotinylated to permit recovery of one strand of the amplified DNA for sequencing using streptavidin coated magnetic beads.

The amplification was performed in a Perkin-Elmer/Cetus thermocycler, and each amplification cycle was as follows:

denaturing 96° C., 30 seconds annealing 55° C., 30 seconds extending 71° C., 50 seconds A total of 40 amplification cycles were used.

The amplified product was then sequenced using an AutoRead Sequencing Kit by mixing it with a fluorescent nested primer having the sequence GATGAGGAAA CTGAGACA [Seq.ID No.: 103] and annealing buffers supplied with the kit, and then sequentially adding extension buffer, and DNA polymerase. The sample was then divided into four portion, and one of the four nucleotide "mixes" from the kit was added to each portion. The portions were then loaded onto individual lanes of a sequencing gel and analyzed with a Pharmacia A.L.F. Sequencer. The results of the sequencing showed that the one base pair deletion results in a premature stop codon, and thus explained the occurrence of the retinoblastoma.

Based on these results, pre-natal testing was suggested in any future pregnancies of either the patient or her parents. No testing or monitoring is necessary for other family members, however, since they did not carry the mutation.

EXAMPLE 4

Amplification primers for use prior to sequencing have been developed for each exon (except exons 15 and 16 which share a common set of primers) and the promoter region of the RB1 gene. These primers are listed in Table 1, together with appropriate amplification parameters. In some cases, the primers are the same as those used in the fragment length/quantity analysis. In other cases, the preferred amplification primers are different. It will be understood, however, that primers of either type can be used for both purposes.

TABLE 1

PCR PRIMERS FOR AMPLIFICATION OF RB1 EXONS

| exon | 5'-primer | 3'-primer | initial denature temp (°C.) time (sec) | Denature temp (°C.) time (sec) | Anneal temp (°C.) time (sec) | Extend temp (°C.) time (sec) | cycles | final ext temp (°C.) time (sec) |
|---|---|---|---|---|---|---|---|---|
| 1 | GCCCCAGTTC CCCACAGACG C [seq 57] | ACCCTTCGCC CAAGAACCCA [seq 14] | 96 180 | 96 50 | 63 50 | 72 60 | 30 | 72 180 |
| 2 | ACTGTGTGGT ATCCTTATTT TG [seq 1] | TCCTCTGGGT AATGGAATTA TT [seq 58] | 96 180 | 94 50 | 58 50 | 71 60 | 40 | 71 180 |
| 3 | ATACAGTTTT AACATAGTAT CCA [seq 3] | AAGTCTATTG AGAGGAAAAT CC [seq 4] | 96 180 | 96 30 | 55 30 | 71 50 | 40 | 71 180 |
| 4 | AGTAGTGATT TGATGTAGAG CT [seq 9] | ATAAAAAATC AGAGTGTAAC CC [seq 40] | 96 180 | 96 30 | 55 30 | 71 50 | 40 | 71 180 |
| 5 | CTACTATGAC TTCTAAATTA CG [seq 5] | ATCAAGATGT TTGAGATTAT TCC [seq 60] | 96 180 | 96 30 | 55 30 | 71 50 | 40 | 71 180 |
| 6 | CACAAAAAGA AACACCCAAA AG [seq 61] | TAATAAGCCA AGCAGAGAAT GA [seq 26] | 96 180 | 94 50 | 58 50 | 71 60 | 40 | 71 180 |
| 7 | TACTCTACCC TGCGATTTTC TC [seq 62] | CCTCCATTTG TTGTATTTTG AC [seq 28] | 96 180 | 94 50 | 58 50 | 71 60 | 40 | 71 180 |
| 8 | TCTAATGAAA CCTAATAAGT A [seq 15] | TGCTCATAAC AAAAGAAGTA A [seq 16] | 94 180 | 94 60 | 50 60 | 71 60 | 30 | 71 180 |
| 9 | ATGGGGGATT GACACCTCTA AC [seq 63] | ATTATCCTCC CTCCACAGTC TC [seq 30] | 96 300 | 94 50 | 61 50 | 71 60 | 40 | 71 180 |
| 10 | TAATGAAATC TGTGCCTCTG [seq 64] | TATCTAAAGG TCACTAAGC [seq 32] | 96 180 | 96 30 | 52 30 | 71 50 | 40 | 71 180 |
| 11 | TATGATTTTA TGAGACAACA GA [seq 65] | TGAACAAATC TGAAACACTA T [seq 34] | 94 300 | 94 30 | 51 30 | 71 50 | 40 | 71 180 |
| 12 | AACTTGGGAG ATTGAAAACA T [seq 66] | AAAAGCAAGA AAAGATTATG G [seq 36] | 94 300 | 94 30 | 51 30 | 71 50 | 40 | 71 180 |
| 13 | TGCTTATGTT CAGTAGTTGT G [seq 7] | TAATGGGGTG GGAGGTAGTT T [seq 8] | 96 180 | 96 30 | 55 30 | 71 50 | 40 | 71 180 |
| 14 | AAAGCAGGAG GATCTCTTGA GC [seq 67] | CCAGGATGAT CTTGATGCC [seq 42] | 96 300 | 94 50 | 57 50 | 71 60 | 40 | 71 180 |
| 15, 16 | CAATGCTGAC ACAAATAAGG TT [seq 49] | CTCCCCCGAC CACCGAAACA C [seq 68] | 96 180 | 94 50 | 58 50 | 71 60 | 40 | 71 180 |
| 17 | ACCTTTCTAC TGTTTTCTTT GT [seq 51] | ATTAGATGGT TTAGGGTGCT C [seq 69] | 96 180 | 96 30 | 55 30 | 71 50 | 40 | 71 180 |
| 18 | TTTTTGTGTG TGGGAAGTA | ATTCTATTCC CTACAGTTTC TT | 96 | 96 | 53 | 71 | 40 | 71 |

TABLE 1-continued

PCR PRIMERS FOR AMPLIFICATION OF RB1 EXONS

| exon | 5'-primer | 3'-primer | initial denature temp (°C.) time (sec) | Denature temp (°C.) time (sec) | Anneal temp (°C.) time (sec) | Extend temp (°C.) time (sec) | cycles | final ext temp (°C.) time (sec) |
|---|---|---|---|---|---|---|---|---|
|  | [seq 70] | [seq 18] | 300 | 50 | 30 | 60 |  | 180 |
| 19 | ATGACAAGCA GTTTTCCTAT T | GCAACATTAT CATTTCCATT TT | 96 | 96 | 55 | 71 | 40 | 71 |
|  | [seq 71] | [seq 54] | 180 | 30 | 30 | 50 |  | 180 |
| 20 | GAAAAGAGTG GTAGAAAAGA GG | TAACAAGTAA GTAGGGAGGA GA | 96 | 94 | 53 | 71 | 40 | 71 |
|  | [seq 43] | [seq 44] | 180 | 50 | 50 | 60 |  | 180 |
| 21 | GGCTAAAAGA AAGAAAATGG | TTACCTATGT TATGTTATGG | 94 | 94 | 51 | 71 | 40 | 71 |
|  | [seq 19] | [seq 20] | 300 | 30 | 30 | 50 |  | 180 |
| 22 | TATGTGCTTC TTACCAGTCA AA | GGAGTCATTT TTGTTGGTGT TG | 96 | 94 | 58 | 71 | 40 | 71 |
|  | [seq 21] | [seq 22] | 180 | 50 | 50 | 60 |  | 180 |
| 23 | CCAGGGTAGG TCAAAAGTAT CC | ATCAAAATAA TCCCCCTCTC AT | 96 | 94 | 58 | 71 | 40 | 71 |
|  | [seq 72] | [seq 24] | 180 | 50 | 50 | 60 |  | 180 |
| 24 | ATGTATTTAT GCTCATCTCT GC | GTGTTTGAAT AACTGCATTT GG | 96 | 94 | 58 | 71 | 40 | 71 |
|  | [seq 73] | [seq 46] | 180 | 50 | 50 | 60 |  | 180 |
| 25 | TCAAACTATA ACTTGAGGTT GC | AAAGAAATTG GTATAAGCCA GG | 96 | 94 | 58 | 71 | 40 | 71 |
|  | [seq 9] | [seq 10] | 180 | 50 | 50 | 60 |  | 180 |
| 26 | TCGAAAGCAT CARAGTTACT GG | ATATAACGAA AAGACTTCTT GC | 96 | 96 | 55 | 71 | 40 | 71 |
|  | [seq 74] | [seq 48] | 180 | 30 | 30 | 50 |  | 180 |
| 27 | ACTTACCCAG TACCATCAAT GC | TCAAGTGGCT TAGGAATCAC CC | 96 | 94 | 58 | 71 | 40 | 71 |
|  | [seq 37] | [seq 38] | 180 | 50 | 50 | 60 |  | 180 |
| prom | ACAGTCACCC ACCAGACTCT TT | ACGTCCCCTG AGAAAAACCG GA | 96 | 96 | 64 | 71 | 30 | 72 |
|  | [seq 75] | [seq 56] | 240 | 50 | 50 | 60 |  | 180 |

EXAMPLE 5

In determining the sequences of exons in the method of the invention, the primers identified above as useful as amplification primers can be used as the sequencing primer. Sequencing primers have been developed for each exon, however, which are nested inside the amplification primers listed in Table 1, i.e., closer to the exon. Table 2 lists these sequencing primers. These sequencing primers could also be used, and in fact in some cases are used, in the fragment analysis as described in Example 1.

TABLE 2

SEQUENCING PRIMERS

| EXON | 3' Sequencing Primer | 5' Sequencing Primer |
|---|---|---|
| 1 | CGCCCGCCCT ACGCACACC [seq 76] | CGTGAGCGCG GGCGGAA [seq 77] |
| 2 | TAGTGATTTG AAGTTGTT [seq 78] | ATGTGCAAAC TATTGAAA [seq 79] |
| 3 | CTATTGAGAG GAAAATCCAG AA [seq 80] | TAACATAGTA GTATCCAGTG T [seq 81] |
| 4 | ATCAGAGTGA AACCCTAA [seq 82] | TTGAAAACGA AATAACAC [seq 39] |
| 5 | AGATGTTTGA GATTATTCCA [seq 83] | TAAATTACGA AAAAATGTTA [seq 84] |
| 6 | CAGAGAATGA GGGAGGAGTA [seq 85] | AAAGAAACAC CCAAAAGATA [seq 25] |
| 7 | TGTCTTATCT TTCCTTCTAT [seq 86] | TGCGATTTTC TCTCATACAA [seq 87] |
| 8 | CATAACAAAA GAAGTAAAT [seq 88] | ATGTTACCAA GATTATTTT [seq 89] |
| 9 | TCCACAGTCT CAAAACATTA [seq 90] | TCAAGAGTCA AGAGATTAGA [seq 29] |
| 10 | TATCTAAAGC AAATCAATC [seq 91] | GTGCTGAGAG ATGTAATGA [seq 31] |
| 11 | AATCTGAAAC ACTATAAA [seq 92] | TGAGACAACA GAAGCATTAT [seq 33] |
| 12 | TGTTAGATAG GAGATTAGT [seq 93] | CCCTTCATTG CTTAACAC [seq 94] |
| 13 | TCTGATTAGA CAGTATCC [seq 95] | GAACTGGAAA GATGCTGC [seq 96] |
| 14 | TCTTGATGCC TTGACCTC [seq 97] | GTGATTTTCT AAAATAGCAG GC [seq 41] |
| 15,16 | ATACTTACTT CTATAAAAAG [seq 98] | CCAAAGAAAC ACACCACATT [seq 99] |
| 17 | AAACACCTCT CACTAACAAT [seq 52] | CTGATAATAA CTTCCAAAAA [seq 100] |
| 18 | TCCCTACAGT TTCTTTAT [seq 101] | TTTGATATGT ACCTGGGA [seq 102] |
| 19 | GATGAGGAAA CTGAGACA [seq 103] | GTGATTCTTA GCCAACTT [seq 104] |
| 20 | AGTAGGGAGG AGAGAAGGTG [seq 105] | CAAAATGAAC AGTAAAAATG [seq 106] |
| 21 | CTATGTTATG TTATGGAT [seq 107] | AAAGAAAGAA AATGGTAT [seq 108] |
| 22 | TGGTGGACCC ATTACATT [seq 109] | ACCAGTCAAA AAGTATTA [seq 110] |
| 23 | TCTCATTCTT TACTACTT [seq 111] | TTGGAAAAAT CTAATGTA [seq 112] |
| 24 | CTTTTATACT TACAATGC [seq 113] | TATGGTTTTT TATTACTA [seq 114] |
| 25 | ATGACCATCT CAGCTACT [seq 115] | TTGCTAACTA TGAAACACT [seq 116] |
| 26 | ATTGTTTATT TCGTTTAC [seq 117] | ATTTGAGTTT TCCATTTA [seq 118] |
| 27 | CTTAGGAATC ACCCAAACA [seq 119] | AGTACCATCA ATGCTGTTA [seq 120] |
| prom | CTGAGAAAAA CCGGACGCG [seq 121] | CCCACCAGAC TCTTTGTA [seq 55] |

The primers used in the present invention are advantageously packaged as kits for the detection of mutations in the RB1 gene. Such a kit may contain a single pair of primers, useful for quantitative amplification of a single exon, or multiple pairs of primers useful for amplification of multiple exons. Such kits may further include amplification and/or sequencing primers for one or more exons. Such kits may also include reagents other than primers for use in the amplification reaction, such a polymerase and buffers, but this is optional.

Preferred kits in accordance with the invention comprise a plurality of primer pairs useful in the coamplification of a plurality of exons of the RB1 gene. Primer pairs in such kits are selected to have a common melting temperature and to produce amplification products having differing lengths.

---

We claim:
1. A method for identifying mutations in a sample retinoblastoma gene comprising the steps of:
  (a) quantitatively amplifying one or more exons of the sample retinoblastoma gene using primers complementary to intron regions immediately flanking each amplified exon;
  (b) determining the lengths of the amplification products for each amplified sample exon and comparing that length to the length of amplification products obtained when a wild-type retinoblastoma gene is amplified using the same primers, whereby differences in length between an amplified sample exon and the corresponding amplified wild-type exon reflect the occurrence on an insertion or deletion mutation in the sample retinoblastoma gene; and
  (c) determining the nucleic acid sequence of each exon identified in step (b) to contain an insertion or deletion mutation, or in the event no insertion or deletion mutations are identified, the nucleic acid sequence of at least one exon of the retinoblastoma gene until all exons have been sequenced or until a mutation has been detected.

2. The method according to claim 1, further comprising the step of determining the quantity of the amplification products and comparing this quantity to that of the corresponding amplified wild-type exon.

3. The method according to claim 1, wherein at least one exon selected from consisting of exons 1, 2, 3, 4, 6, 7, 8, 9, 10, 11, 12, 13, 14, 15, 16, 17, 18, 19, 20, 21, 22, 23 and 24 is sequenced.

4. The method according to claim 1, wherein the lengths of the amplification products for each amplified sample exon are determined by electrophoresis on a gel having a resolution of one-base.

5. The method according to claim 1, wherein the lengths of the amplification products for each amplified sample exon are determined by electrophoresis on a polyacrylamide gel having a resolution of one-base.

6. The method according to claim 1, wherein at least two of the exons of the sample RB1 gene are coamplifed in a single reaction.

7. The method according to claim 1, wherein at least three of the exons of the sample RB1 gene are coamplifed in a single reaction.

8. The method according to claim 7, wherein the primers for the coamplified exons of the RB1 gene are selected to provide amplified fragments of different lengths.

9. The method according to claim 8, wherein lengths of the amplified fragments differ by at least 5 bases.

10. The method according to claim 1, wherein at least exon 1 of the RB1 gene is quantitatively amplified, and wherein the primers used are GCCCCAGTTC CCCACAGAC [Seq ID No.: 13] and ACCCCTCGCC CAAGAACCCA [Seq ID No.: 14].

11. The method according to claim 1, wherein at least exon 2 of the RB1 gene is quantitatively amplified, and wherein the primers used are ACTGTGTGGT ATCCTTATTT TG [Seq ID No.: 1] and ATAGTGATTT GAAGTTGGTT TTA [Seq ID No.: 2].

12. The method according to claim 1, wherein at least exon 3 of the RB1 gene is quantitatively amplified, and wherein the primers used are ATACAGTTTT AACATAGTAT CCA [Seq ID No.: 3] and AAGTCTATTG AGAGGAAAAT CC [Seq ID No.: 4].

13. The method according to claim 1, wherein at least exon 4 of the RB1 gene is quantitatively amplified, and wherein the primers used are TTGAAAACGA AATAACAC [Seq ID No.: 39] and ATAAAAAATC AGAGTGTAAC CC [Seq ID No.: 40].

14. The method according to claim 1, wherein at least exon 5 of the RB1 gene is quantitatively amplified, and wherein the primers used are CTACTATGAC TTCTAAATTA CG [Seq ID No.: 5] and TCAAGATGTT TGAGATTATT CC [Seq ID No.: 6].

15. The method according to claim 1, wherein at least exon 6 of the RB1 gene is quantitatively amplified, and wherein the primers used are AAAGAAACAC CCAAAAGATA [Seq ID No.: 25] and TAATAAGCCA AGCAGAGAAT GA [Seq ID No.: 26].

16. The method according to claim 1, wherein at least exon 7 of the RB1 gene is quantitatively amplified, and wherein the primers used are TTATGGATAT ACTCTACCCT GC [Seq ID No.: 27] and CCTCCATTTG TTGTATTTTG AC [Seq ID No.: 28].

17. The method according to claim 1 wherein at least exon 8 of the RB1 gene is quantitatively amplified, and wherein the primers used are TCTAATGAAA CCTAATAAGT A [Seq ID No.: 15] and TGCTCATAAC AAAAGAAGTA A [Seq ID No.: 16].

18. The method according to claim 1, wherein at least exon 9 of the RB1 gene is quantitatively amplified, and wherein the primers used are TCAAGAGTCA AGAGATTAGA [Seq ID No.: 29] and ATTATCCTCC CTCCACAGTC TC [Seq ID No.: 30].

19. The method according to claim 1, wherein at least exon 10 of the RB1 gene is quantitatively amplified, and wherein the primers used are GTGCTGAGAG ATGTAATGA [Seq ID No.: 31] and TATCTAAAGG TCACTAAGC [Seq ID No.: 32].

20. The method according to claim 1, wherein at least exon 11 of the RB1 gene is quantitatively amplified, and wherein the primers used are TGAGACAACA GAAGCATTAT [Seq ID No.: 33] and TGAACAAATC TGAAACACTAT [Seq ID No.: 34 ].

21. The method according to claim 1, wherein at least exon 12 of the RB1 gene is quantitatively amplified, and wherein the primers used are CTCCCTTCAT TGCTTAACAC AT [Seq ID No.: 35] and AAAAGCAAGA AAAGATTATG G [Seq ID No.: 36].

22. The method according to claim 1, wherein at least exon 13 of the RB1 gene is quantitatively amplified, and wherein the primers used are TGCTTATGTT CAGTAGTTGT G [Seq ID No.: 7] and TAATGGGGTG GGAGGTAGTT T [Seq ID No.: 8].

23. The method according to claim 1, wherein at least exon 14 of the RB1 gene is quantitatively amplified, and wherein the primers used are GTGATTTTCT AAAATAGCAG GC [Seq ID No.: 41 ] and CCAGGATGAT CTTGATGCC [Seq ID No.: 42].

24. The method according to claim 1, wherein at least exons 15 and 16 of the RB1 gene are quantitatively amplified using a single pair of primers, and wherein the primers used are CAATGCTGAC ACAAATAAGG TT [Seq ID No.: 49] and CCCCCGACCA AAGAAACACA [Seq ID No.: 50].

25. The method according to claim 1, wherein at least exon 17 of the RB1 gene is quantitatively amplified, and wherein the primers used are ACCTTTCTAC TGTTTTCTTT GT [Seq ID No.: 51] and AAACACCTCT CACTAACAAT [Seq ID No.: 52].

26. The method according to claim 1, wherein at least exon 18 of the RB1 gene is quantitatively amplified, and wherein the primers used are TTTTTGTGTG TGGGAAGTAC A [Seq ID No.: 17] and ATTCTATTCC CTACAGTTTC TT [Seq ID No.: 18].

27. The method according to claim 1, wherein at least exon 19 of the RB1 gene is quantitatively amplified, and wherein the primers used are TGTATAATCT GTGATTCTTA GC [Seq ID No.: 53] and GCAACATTAT CATTTCCATT TT [Seq ID No.: 54].

28. The method according to claim 1, wherein at least exon 20 of the RB1 gene is quantitatively amplified, and wherein the primers used are GAAAAGAGTG GTAGAAAAGA GG [Seq ID No.: 43] and TAACAAGTAA GTAGGGAGGA GA [Seq ID No.: 44].

29. The method according to claim 1, wherein at least exon 21 of the RB1 gene is quantitatively amplified, and wherein the primers used are GGCTAAAAGA AAGAAAATGG [Seq ID No.: 19] and TTACCTATGT TATGTTATGG [Seq ID No.: 20].

30. The method according to claim 1, wherein at least exon 22 of the RB1 gene is quantitatively amplified, and wherein the primers used are TATGTGCTTC TTACCAGTCA AA [Seq ID No.: 21] and GGAGTCATTT TTGTTGGTGT TG [Seq ID No.: 22].

31. The method according to claim 1, wherein at least exon 23 of the RB1 gene is quantitatively amplified, and wherein the primers used are AATCTAATGT AATGGGTCCA CC [Seq ID No.: 23] and ATCAAAATAA TCCCCCTCTC AT [Seq ID No.: 24].

32. The method according to claim 1, wherein at least exon 24 of the RB1 gene is quantitatively amplified, and wherein the primers used are GTATTTATGC TCATCTCTGC [Seq ID No.: 45] and GTGTTTGAAT AACTGCATTT GG [Seq ID No.: 46].

33. The method according to claim 1, wherein at least exon 25 of the RB1 gene is quantitatively amplified, and wherein the primers used are TCAAACTATA ACTTGAGGTT GC [Seq ID No.: 9] and AAAGAAATTG GTATAAGCCA GG [Seq ID No.: 10].

34. The method according to claim 1, wherein at least exon 26 of the RB1 gene is quantitatively amplified, and wherein the primers used are CGAAAGCATC ATAGTTACTG G [Seq ID No.: 47] and ATATAACGAA AAGACTTCTT GC [Seq ID No.: 48].

35. The method according to claim 1, wherein at least exon 27 of the RB1 gene is quantitatively amplified, and wherein the primers used are ACTTACCCAG TACCATCAAT GC [Seq ID No.: 37] and TCAAGTGGCT TAGGAATCAC CC [Seq ID No.: 38].

36. The method according to claim 1, wherein exons 2, 3, 5, 13 and 25 of the sample RB1 gene are coamplifed in a single reaction.

37. The method according to claim 36, wherein the primers employed for the coamplification are as follows:

for exon 2, Seq.ID No.: 1 and Seq.ID No.: 2;

for exon 3, Seq.ID No.: 3 and Seq.ID No.: 4;

for exon 5, Seq.ID No.: 5 and Seq.ID No.: 6;

for exon 13, Seq.ID No.: 7 and Seq.ID No.: 8; and for exon 25, Seq.ID No.: 9 and Seq.ID No.: 10.

38. The method according to claim 1, wherein exons 1, 8, 18, 21, 22, and 23 of the sample RB1 gene are coamplified in a single reaction.

39. The method according to claim 38, wherein the primers employed for the coamplification are as follows:

for exon 1, Seq.ID No.: 13 and Seq.ID No.: 14;

for exon 8, Seq.ID No.: 15 and Seq.ID No.: 16;

for exon 18, Seq.ID No.: 17 and Seq.ID No.: 18;

for exon 21, Seq.ID No.: 19 and Seq.ID No.: 20;

for exon 22, Seq.ID No.: 21 and Seq.ID No.: 22; and for exon 23, Seq.ID No.: 23 and Seq.ID No.: 24.

40. The method according to claim 1, wherein exons 6, 7, 8, 9, 10, 11, 12, and 27 of the sample RB1 gene are coamplified in a single reaction.

41. The method according to claim 40, wherein the primers employed for the coamplification are as follows:

for exon 6, Seq.ID No.: 25 and Seq.ID No.: 26;

for exon 7, Seq.ID No.: 27 and Seq.ID No.: 28;

for exon 9, Seq.ID No.: 29 and Seq.ID No.: 30;

for exon 10, Seq.ID No.: 31 and Seq.ID No.: 32;

for exon 11, Seq.ID No.: 33 and Seq.ID No.: 34;

for exon 12, Seq.ID No.: 35 and Seq.ID No.: 36; and for exon 27, Seq.ID No: 37 and Seq.ID No.: 38.

42. The method according to claim 1, wherein exons 4, 14, 20, 24 and 26 of the sample RB1 gene are coamplified in a single reaction.

43. The method according to claim 42, wherein the primers employed for the coamplification are as follows:

for exon 4, Seq.ID No.: 39 and Seq.ID No.: 40;

for exon 14, Seq.ID No.: 41 and Seq.ID No.: 42;

for exon 20, Seq.ID No.: 43 and Seq.ID No.: 44;

for exon 24, Seq.ID No.: 45 and Seq.ID No.: 46; and for exon 26, Seq.ID No.: 47 and Seq.ID No.: 48.

44. The method according to claim 1, wherein exons 15, 16, 17, and 19 of the sample RB1 gene are coamplified in a single reaction.

45. The method according to claim 44, wherein the primers employed for the coamplification are as follows:

for exons 15 and 16, Seq.ID No.: 49 and Seq.ID No.: 50;

for exon 17, Seq.ID No.: 51 and Seq.ID No.: 52; and for exon 19, Seq.ID No.: 53 and Seq.ID NO.: 54.

46. The method for genetic screening of family members of an individual diagnosed as having retinoblastoma, comprising the steps of:

(a) obtaining a patient blood sample from the diagnosed individual;

(b) quantitatively amplifying at least one exon of the retinoblastoma gene in cells from the patient blood sample using primers complementary to intron regions immediately flanking each exon amplified;

(c) determining the length of the amplification product for each exon amplified and comparing that length to the length of amplification products obtained when a wild-type retinoblastoma gene is amplified using the same primers, whereby differences in length between an amplified sample exon and the corresponding amplified wild-type exon reflect the occurrence of an inherited insertion or deletion mutation in the retinoblastoma gene of the diagnosed individual; and (d) if an inherited mutation is identified, obtaining blood samples from the biological parents of the diagnosed individual; quantitatively amplifying the exon of the retinoblastoma gene found to contain an insertion or deletion mutation in the patient blood sample in cells from the parent blood samples using the same primers used to amplify the exons in the patient blood sample; and determining the length of the amplification product for the exon in the amplified parent blood samples and comparing that length to the length of amplification products obtained when the patient blood sample was amplified.

47. The method according to claim 46, further comprising the step of determining the quantity of the amplification products and comparing this quantity to that of the corresponding amplified wild-type exon.

48. The method according to claim 46, further comprising the step of determining the sequence of the exon containing the inherited mutation.

49. The method according to claim 46, wherein the length of the amplified fragments is determined by electrophoresis on a gel having a resolution capable of detecting length differences of one base pair.

50. The method according to claim 46, wherein the length of the amplified fragments is determined by electrophoresis on a polyacrylamide gel having a resolution capable of detecting length differences of one base pair.

51. The method according to claim 46, wherein the exons of the RB1 gene in cells from the patient blood sample are coamplifed in groups of three or more exons per amplification reaction.

52. The method according to claim 46, wherein at least one parent is found to carry the mutation found in the patient, further comprising the steps of obtaining aunt/uncle blood samples from the siblings of the parent found to carry the mutation;

quantitatively amplifying the exon of the RB1 gene found to contain an insertion or deletion mutation in the patient blood sample in cells from the aunt/uncle blood samples using the same primers used to amplify the exons in the patient blood sample; and determining the length of the amplification product for the exon in the amplified aunt/uncle blood samples and comparing that length to the length of amplification products obtained when the patient blood sample was amplified.

53. The method according to claim 46, wherein at least exon 1 of the RB1 gene is quantitatively amplified, and wherein the primers used are GCCCCAGTTC CCCACAGAC [Seq ID No.: 13] and ACCCCTCGCC CAAGAACCCA [Seq ID No.: 14].

54. The method according to claim 46, wherein at least exon 2 of the RB1 gene is quantitatively amplified, and wherein the primers used are ACTGTGTGGT ATCCTTATTT TG [Seq ID No.: 1] and ATAGTGATTT GAAGTTGGTT TTA [Seq ID No.: 2].

55. The method according to claim 46, wherein at least exon 3 of the RB1 gene is quantitatively amplified, and wherein the primers used are ATACAGTTTT AACATAGTAT CCA [Seq ID No.: 3] and AAGTCTATTG AGAGGAAAAT CC [Seq ID No.: 4].

56. The method according to claim 46, wherein at least exon 4 of the RB1 gene is quantitatively amplified, and wherein the primers used are TTGAAAACGA AATAACAC [Seq ID No.: 39] and ATAAAAAATC AGAGTGTAAC CC [Seq ID No.: 40].

57. The method according to claim 46, wherein at least exon 5 of the RB1 gene is quantitatively amplified, and wherein the primers used are CTACTATGAC TTCTAAATTA CG [Seq ID No.: 5] and TCAAGATGTT TGAGATTATT CC [Seq ID No.: 6].

58. The method according to claim 46, wherein at least exon 6 of the RB1 gene is quantitatively amplified, and wherein the primers used are AAAGAAACAC CCAAAAGATA [Seq ID No.: 25] and TAATAAGCCA AGCAGAGAAT GA [Seq ID No.: 26].

59. The method according to claim 46, wherein at least exon 7 of the RB1 gene is quantitatively amplified, and wherein the primers used are TTATGGATAT ACTCTACCCT GC [Seq ID No.: 27] and CCTCCATTTG TTGTATTTTG AC [Seq ID No.: 28].

60. The method according to claim 46, wherein at least exon 8 of the RB1 gene is quantitatively amplified, and wherein the primers used are TCTAATGAAA CCTAATAAGT A [Seq ID No.: 15] and TGCTCATAAC AAAAGAAGTA A [Seq ID No.: 16].

61. The method according to claim 46, wherein at least exon 9 of the RB1 gene is quantitatively amplified, and wherein the primers used are TCAAGAGTCA AGAGATTAGA [Seq ID No.: 29] and ATTATCCTCC CTCCACAGTC TC [Seq ID No.: 30].

62. The method according to claim 46, wherein at least exon 10 of the RB1 gene is quantitatively amplified, and wherein the primers used are GTGCTGAGAG ATGTAATGA [Seq ID No.: 31] and TATCTAAAGG TCACTAAGC [Seq ID No.: 32].

63. The method according to claim 46, wherein at least exon 11 of the RB1 gene is quantitatively amplified, and wherein the primers used are TGAGACAACA GAAGCATTAT [Seq ID No.: 33] and TGAACAAATC TGAAACACTAT [Seq ID No.: 34].

64. The method according to claim 46, wherein at least exon 12 of the RB1 gene is quantitatively amplified, and wherein the primers used are CTCCCTTCAT TGCTTAACAC AT [Seq ID No.: 35] and AAAAGCAAGA AAAGATTATG G [Seq ID No.: 36].

65. The method according to claim 46, wherein at least exon 13 of the RB1 gene is quantitatively amplified, and wherein the primers used are TGCTTATGTT CAGTAGTTGT G [Seq ID No.: 7] and TAATGGGGTG GGAGGTAGTT T [Seq ID No.: 8].

66. The method according to claim 46, wherein at least exon 14 of the RB1 gene is quantitatively amplified, and wherein the primers used are GTGATTTTCT AAAATAGCAG GC [Seq ID No.: 41] and CCAGGATGAT CTTGATGCC [Seq ID No.: 42].

67. The method according to claim 46, wherein at least exons 15 and 16 of the RB1 gene are quantitatively amplified using a single pair of primers, and wherein the primers used are CAATGCTGAC ACAAATAAGG TT [Seq ID No.: 49] and CCCCCGACCA AAGAAACACA [Seq ID No.: 50].

68. The method according to claim 46, wherein at least exon 17 of the RB1 gene is quantitatively amplified, and wherein the primers used are ACCTTTCTAC TGTTTTCTTT GT [Seq ID No.: 51] and AAACACCTCT CACTAACAAT [Seq ID No.: 52].

69. The method according to claim 46, wherein at least exon 18 of the RB1 gene is quantitatively amplified, and wherein the primers used are TTTTTGTGTG TGGGAAGTAC A [Seq ID No.: 17] and ATTCTATTCC CTACAGTTTC TT [Seq ID No.: 18].

70. The method according to claim 46, wherein at least exon 19 of the RB1 gene is quantitatively amplified, and wherein the primers used are TGTATAATCT GTGATTCTTA GC [Seq ID No.: 53] and GCAACATTAT CATTTCCATT TT [Seq ID No.: 54].

71. The method according to claim 46, wherein at least exon 20 of the RB1 gene is quantitatively amplified, and wherein the primers used are GAAAAGAGTG GTAGAAAAGA GG [Seq ID No.: 43] and TAACAAGTAA GTAGGGAGGA GA [Seq ID No.: 44].

72. The method according to claim 46, wherein at least exon 21 of the RB1 gene is quantitatively amplified, and wherein the primers used are GGCTAAAAGA AAGAAAATGG [Seq ID No.: 19] and TTACCTATGT TATGTTATGG [Seq ID No.: 20].

73. The method according to claim 46, wherein at least exon 22 of the RB1 gene is quantitatively amplified, and wherein the primers used are TATGTGCTTC TTACCAGTCA AA [Seq ID No.: 21] and GGAGTCATTT TTGTTGGTGT TG [Seq ID No.: 22].

74. The method according to claim 46, wherein at least exon 23 of the RB1 gene is quantitatively amplified, and wherein the primers used are AATCTAATGT AATGGGTCCA CC [Seq ID No.: 23] and ATCAAAATAA TCCCCCTCTC AT [Seq ID No.: 24].

75. The method according to claim 46, wherein at least exon 24 of the RB1 gene is quantitatively amplified, and wherein the primers used are GTATTTATGC TCATCTCTGC [Seq ID No.: 45] and GTGTTTGAAT AACTGCATTT GG [Seq ID No.: 46].

76. The method according to claim 46, wherein at least exon 25 of the RB1 gene is quantitatively amplified, and wherein the primers used are TCAAACTATA ACTTGAGGTT GC [Seq ID No.: 9] and AAAGAAATTG GTATAAGCCA GG [Seq ID No.: 10].

77. The method according to claim 46, wherein at least exon 26 of the RB1 gene is quantitatively amplified, and wherein the primers used are CGAAAGCATC ATAGTTACTG G [Seq ID No.: 47] and ATATAACGAA AAGACTTCTT GC [Seq ID No.: 48].

78. The method according to claim 46, wherein at least exon 27 of the RB1 gene is quantitatively amplified, and wherein the primers used are ACTTACCCAG TACCATCAAT GC [Seq ID No.: 37] and TCAAGTGGCT TAGGAATCAC CC [Seq ID No.: 38].

79. The method according to claim 46, wherein exons 2, 3, 5, 13 and 25 of the sample RB1 gene are coamplifed in a single reaction.

80. The method according to claim 79, wherein the primers employed for the coamplification are as follows:

for exon 2, Seq.ID No.: 1 and Seq.ID No.: 2;

for exon 3, Seq.ID No.: 3 and Seq.ID No.: 4;

for exon 5, Seq.ID No.: 5 and Seq.ID No.: 6;

for exon 13, Seq.ID No.: 7 and Seq.ID No.: 8; and for exon 25, Seq.ID No.: 9 and Seq.ID No.: 10.

81. The method according to claim 46, wherein exons 1, 8, 18, 21, 22, and 23 of the sample RB1 gene are coamplified in a single reaction.

82. The method according to claim 81, wherein the primers employed for the coamplification are as follows:

for exon 1, Seq.ID No.: 13 and Seq.ID No.: 14;

for exon 8, Seq.ID No.: 15 and Seq.ID No.: 16;

for exon 18, Seq.ID No.: 17 and Seq.ID No.: 18;

for exon 21, Seq.ID No.: 19 and Seq.ID No.: 20;

for exon 22, Seq.ID No.: 21 and Seq. I.D No.: 22; and for exon 23, Seq.ID No.: 23 and Seq.ID No.: 24.

83. The method according to claim 46, wherein exons 6, 7, 8, 9, 10, 11, 12, and 27 of the sample RB1 gene are coamplified in a single reaction.

84. The method according to claim 83, wherein the primers employed for the coamplification are as follows:

for exon 6, Seq.ID No.: 25 and Seq.ID No.: 26;

for exon 7, Seq.ID No.: 27 and Seq.ID No.: 28;

for exon 9, Seq.ID No.: 29 and Seq.ID No.: 30;

for exon 10, Seq.ID No.: 31 and Seq.ID No.: 32;

for exon 11, Seq.ID. No.: 33 and Seq.ID No.: 34;

for exon 12, Seq.ID No.: 35 and Seq.ID No.: 36; and for exon 27, Seq.ID No.: 3.7 and Seq.ID No.: 38.

85. The method according to claim 46, wherein exons 4, 14, 20, 24 and 26 of the sample RB1 gene are coamplified in a single reaction.

86. The method according to claim 85, wherein the primers employed for the coamplification are as follows:

for exon 4, Seq.ID No.: 39 and Seq.ID No.: 40;

for exon 14, Seq.ID No.: 41 and Seq.ID No.: 42;

for exon 20, Seq.ID No.: 43 and Seq.ID No.: 44;

for exon 24, Seq.ID No.: 45 and Seq.ID No.: 46; and for exon 26, Seq.ID No.: 47 and Seq.ID No.: 48.

87. The method according to claim 46, wherein exons 15, 16, 17, and 19 of the sample RB1 gene are coamplified in a single reaction.

88. The method according to claim 87, wherein the primers employed for the coamplification are as follows:

for exons 15 and 16, Seq.ID No.: 49 and Seq.ID No.: 50;

for exon 17, Seq.ID No.: 51 and Seq.ID No.: 52; and for exon 19, Seq.ID No.: 53 and Seq.ID No.: 54.

89. The method for generating a report on the nature of a mutation causing retinoblastoma in a patient, comprising the steps of (a) obtaining a sample of patient tissue, (b) quantitatively amplifying one or more exons of the sample retinoblastoma gene using primers complementary to intron regions immediately flanking each amplified exon;

(c) determining the lengths of the amplification products for each amplified sample exon and comparing that length to the length of amplification products obtained when a wild-type retinoblastoma gene is amplified using the same primers, whereby differences in length between an amplified sample exon and the corresponding amplified wild-type exon reflect the occurrence on an insertion or deletion mutation in the sample retinoblastoma gene;

(d) determining the nucleic acid sequence of each exon identified in step (c) to contain an insertion or deletion mutation, or in the event no insertion or deletion mutations are identified, the nucleic acid sequence of at least one exon until all exons have been sequenced or a mutation has been detected; and (e) generating a report identifying the exon in which the mutation is located.

90. A method according to claim 89, wherein the report is a printed report.

91. A method according to claim 89, wherein the report is an electronic communication.

92. A method according to claim 89, wherein the report is a data entry in a computer record relating to the patient.

93. A method for identifying mutations in a plurality of samples containing the retinoblastoma gene comprising the steps of:

(a) quantitatively amplifying one or more exons of the retinoblastoma gene of each sample using primers complementary to intron regions immediately flanking each amplified exon;

(b) determining the lengths of the amplification products for each amplified exon of each sample and comparing that length to the length of amplification products obtained when a wild-type retinoblastoma gene is amplified using the same primers, whereby differences in length between an amplified sample exon and the corresponding amplified wild-type exon reflect the occurrence on an insertion or deletion mutation in the sample retinoblastoma gene; and (c) for each sample for which no insertion or deletion mutations is identified, determining the complete the nucleic acid sequence of at least one exon of the retinoblastoma gene.

94. The method according to claim 93, further comprising the step of determining the quantity of the amplification products for each sample and comparing this quantity to that of the corresponding amplified wild-type exon.

95. The method according to claim 93, wherein at least one exon selected from consisting of exons 1, 2, 3, 4, 6, 7, 8, 9, 10, 11, 12, 13, 14, 15, 16, 17, 18, 19, 20, 21, 22, 23 and 24 is sequenced for each sample.

96. The method according to claim 93, wherein the lengths of the amplification products for each amplified exon of each sample are determined by electrophoresis on a gel having a resolution of one-base.

97. The method according to claim 93, wherein the lengths of the amplification products for each amplified exon of each sample are determined by electrophoresis on a polyacrylamide gel having a resolution of one-base.

98. The method according to claim 93, wherein at least two of the exons of the retinoblastoma gene of each sample are coamplified in a single reaction.

99. The method according to claim 93, wherein at least three exons of the retinoblastoma gene of each sample are coamplified in a single reaction.

100. The method according to claim 99, wherein the primers for the coamplified exons of the retinoblastoma gene are selected to provide amplified fragments of different lengths.

101. The method according to claim 100, wherein lengths of the amplified fragments differ by at least 5 bases.

102. The method according to claim 93, wherein at least exon 1 of the retinoblastoma gene is quantitatively amplified, and wherein the primers used are GCCCCAGTTC CCCACAGAC [Seq ID No.: 13] and ACCCCTCGCC CAAGAACCCA [Seq ID No. 14].

103. The method according to claim 93, wherein at least exon 2 of the RB1 gene is quantitatively amplified, and wherein the primers used are ACTGTGTGGT ATCCTTATTT TG [Seq ID No.: 1] and ATAGTGATTT GAAGTTGGTT TTA [Seq ID No.: 2].

104. The method according to claim 93, wherein at least exon 3 of the RB1 gene is quantitatively amplified, and wherein the primers used are ATACAGTTTT AACATAGTAT CCA [Seq ID No.: 3] and AAGTCTATTG AGAGGAAAAT CC [Seq ID No.: 4].

105. The method according to claim 93, wherein at least exon 4 of the RB1 gene is quantitatively amplified, and wherein the primers used are TTGAAAACGA AATAACAC [Seq ID No.: 39] and ATAAAAAATC AGAGTGTAAC CC [Seq ID No.: 40].

106. The method according to claim 93, wherein at least exon 5 of the RB1 gene is quantitatively amplified, and wherein the primers used are CTACTATGAC TTCTAAATTA CG [Seq ID No.: 5] and TCAAGATGTT TGAGATTATT CC [Seq ID No.: 6].

107. The method according to claim 93, wherein at least exon 6 of the RB1 gene is quantitatively amplified, and wherein the primers used are AAAGAAACAC CCAAAAGATA [Seq ID No.: 25] and TAATAAGCCA AGCAGAGAAT GA [Seq ID No.: 26].

108. The method according to claim 93, wherein at least exon 7 of the RB1 gene is quantitatively amplified, and wherein the primers used are TTATGGATAT ACTCTACCCT GC [Seq ID No.: 27] and CCTCCATTTG TATGTTATGG AC [Seq ID No.: 28].

109. The method according to claim 93, wherein at least exon 8 of the RB1 gene is quantitatively amplified, and wherein the primers used are TCTAATGAAA CCTAATAAGT A [Seq ID No.: 15] and TGCTCATAAC AAAAGAAGTA A [Seq ID No.: 16].

110. The method according to claim 93, wherein at least exon 9 of the RB1 gene is quantitatively amplified, and wherein the primers used are TCAAGAGTCA AGAGATTAGA [Seq ID No.: 29] and ATTATCCTCC CTCCACAGTC TC [Seq ID No.: 30].

111. The method according to claim 93, wherein at least exon 10 of the RB1 gene is quantitatively amplified, and wherein the primers used are GTGCTGAGAG ATGTAATGA [Seq ID No.: 31] and TATCTAAAGG TCACTAAGC [Seq ID No.: 32].

112. The method according to claim 93, wherein at least exon 11 of the RB1 gene is quantitatively amplified, and wherein the primers used are TGAGACAACA GAAGCATTAT [Seq ID No.: 33] and TGAACAAATC TGAAACACTA T [Seq ID No.: 34].

113. The method according to claim 93, wherein at least exon 12 of the RB1 gene is quantitatively amplified, and wherein the primers used are CTCCCTTCAT TGCTTAACAC AT [Seq ID No.: 35] and AAAAGCAAGA AAAGATTATG G [Seq ID No.: 36].

114. The method according to claim 93, wherein at least exon 13 of the RB1 gene is quantitatively amplified, and wherein the primers used are TGCTTATGTT CAGTAGTTGT G [Seq ID No.: 7] and TAATGGGGTG GGAGGTAGTT T [Seq ID No.: 8].

115. The method according to claim 93, wherein at least exon 14 of the RB1 gene is quantitatively amplified, and wherein the primers used are GTGATTTTCT AAAATAGCAG GC [Seq ID No.: 41] and CCAGGATGAT CTTGATGCC [Seq ID No.: 42].

116. The method according to claim 93, wherein at least exons 15 and 16 of the RB1 gene are quantitatively amplified using a single pair of primers, and wherein the primers used are CAATGCTGAC ACAAATAAGG TT [Seq ID No.: 49] and CCCCCGACCA AAGAAACACA [Seq ID No.: 50].

117. The method according to claim 93, wherein at least exon 17 of the RB1 gene is quantitatively amplified, and wherein the primers used are ACCTTTCTAC TGTTTTCTTT GT [Seq ID No.: 51 ] and AAACACCTCT CACTAACAAT [Seq ID No.: 52].

118. The method according to claim 93, wherein at least exon 18 of the RB1 gene is quantitatively amplified, and wherein the primers used are TTTTTGTGTG TGGGAAGTAC A [Seq ID No.: 17] and ATTCTATTCC CTACAGTTTC TT [Seq ID No.: 18].

119. The method according to claim 93, wherein at least exon 19 of the RB1 gene is quantitatively amplified, and wherein the primers used are TGTATAATCT GTGATTCTTA GC [Seq ID No.: 53] and GCAACATTAT CATTTCCATT TT [Seq ID No.: 54].

120. The method according to claim 93, wherein at least exon 20 of the RB1 gene is quantitatively amplified, and wherein the primers used are GAAAAGAGTG GTAGAAAAGA GG [Seq ID No.: 43] and TAACAAGTAA GTAGGGAGGA GA [Seq ID No.: 44].

121. The method according to claim 93, wherein at least exon 21 of the RB1 gene is quantitatively amplified, and wherein the primers used are GGCTAAAAGA AAGAAAATGG [Seq ID No.: 19] and TTACCTATGT TATGTTATGG [Seq ID No.: 20].

122. The method according to claim 93, wherein at least exon 22 of the RB1 gene is quantitatively amplified, and wherein the primers used are TATGTGCTTC TTACCAGTCA AA [Seq ID No.: 21] and GGAGTCATTT TTGTTGGTGT TG [Seq ID No.: 22].

123. The method according to claim 93, wherein at least exon 23 of the RB1 gene is quantitatively amplified, and wherein the primers used are AATCTAATGT AATGGGTCCA CC [Seq ID No.: 23] and ATCAAAATAA TCCCCCTCTC AT [Seq ID No.: 24].

124. The method according to claim 93, wherein at least exon 24 of the RB1 gene is quantitatively amplified, and wherein the primers used are GTATTTATGC TCATCTCTGC [Seq ID No.: 45] and GTGTTTGAAT AACTGCATTr GG [Seq ID No.: 46].

125. The method according to claim 93, wherein at least exon 25 of the RB1 gene is quantitatively amplified, and wherein the primers used are TCAAACTATA ACTTGAGGTT GC [Seq ID No.: 9] and AAAGAAATTG GTATAAGCCA GG [Seq ID No.: 10].

126. The method according to claim 93, wherein at least exon 26 of the RB1 gene is quantitatively amplified, and wherein the primers used are CGAAAGCATC ATAGTTACTG G [Seq ID No.: 47] and ATATAACGAA AAGACTTCTT GC [Seq ID No.: 48].

127. The method according to claim 93, wherein at least exon 27 of the RB1 gene is quantitatively amplified, and wherein the primers used are ACTTACCCAG TACCATCAAT GC [Seq ID No.: 37] and TCAAGTGGCT TAGGAATCAC CC [Seq ID No.: 38].

128. The method according to claim 93, wherein exons 2, 3, 5, 13 and 25 of the sample RB1 gene are coamplified in a single reaction.

129. The method according to claim 128, wherein the primers employed for the coamplification are as follows:

for exon 2, Seq.ID No.: 1 and Seq.ID No.: 2;

for exon 3, Seq.ID No.: 3 and Seq.ID No.: 4;

for exon 5, Seq.ID No.: 5 and Seq.ID No.: 6;

for exon 13, Seq.ID No.: 7 and Seq.ID No.: 8; and for exon 25, Seq.ID No.: 9 and Seq.ID No.: 10.

130. The method according to claim 93, wherein exons 1, 8, 18, 21, 22, and 23 of the sample RB1 gene are coamplified in a single reaction.

131. The method according to claim 168, wherein the primers employed for the coamplification are as follows:

for exon 1, Seq.ID No.: 13 and Seq.ID No.: 14;

for exon 8, Seq.ID No.: 15 and Seq.ID No.: 16;

for exon 18, Seq.ID No.: 17 and Seq.ID No.: 18;

for exon 21, Seq.ID No.: 19 and Seq.ID No.: 20;

for exon 22, Seq.ID No.: 21 and Seq.ID No.: 22; and for exon 23, Seq.ID No.: 23 and Seq.ID No.: 24.

132. The method according to claim 93, wherein exons 6, 7, 8, 9, 10, 11, 12, and 27 of the sample RB1 gene are coamplified in a single reaction.

133. The method according to claim 132, wherein the primers employed for the coamplification are as follows:

for exon 6, Seq.ID No.: 25 and Seq.ID No.: 26;

for exon 7, Seq.ID No.: 27 and Seq.ID No.: 28;

for exon 9, Seq.ID No.: 29 and Seq.ID No.: 30;

for exon 10, Seq.ID No.: 31 and Seq.ID No.: 32;

for exon 11, Seq.ID No.: 33 and Seq.ID No.: 34;

for exon 12, Seq.ID No.: 35 and Seq.ID No.: 36; and for exon 27, Seq.ID No.: 37 and Seq.ID No.: 38.

134. The method according to claim 93, wherein exons 4, 14, 20, 24 and 26 of the sample RB1 gene are coamplified in a single reaction.

135. The method according to claim 134, wherein the primers employed for the coamplification are as follows:

for exon 4, Seq.ID No.: 39 and Seq.ID No.: 40;

for exon 14, Seq.ID No.: 41 and Seq.ID No.: 42;

for exon 20, Seq.ID No.: 43 and Seq.ID No.: 44;

for exon 24, Seq.ID No.: 45 and Seq.ID No.: 46; and for exon 26, Seq.ID No.: 47 and Seq.ID No.: 48.

136. The method according to claim 93, wherein exons 15, 16, 17, and 19 of the sample RB1 gene are coamplified in a single reaction.

137. The method according to claim 136, wherein the primers employed for the coamplification are as follows:

for exons 15 and 16, Seq.ID No.: 49 and Seq.ID No.: 50;

for exon 17, Seq.ID No.: 51 and Seq.ID No.: 52; and for exon 19, Seq.ID No.: 53 and Seq.ID No.: 54.

\* \* \* \* \*